United States Patent
Hafer et al.

(10) Patent No.: US 7,386,341 B2
(45) Date of Patent: Jun. 10, 2008

(54) INSTRUMENT AND METHOD FOR DELIVERY OF ANAESTHETIC DRUGS

(75) Inventors: Fred Hafer, Shillington, PA (US); Jeffrey M. Vitullo, Pottstown, PA (US); Richard L. Harding, Reinholds, PA (US); Mark J. Spinka, Reading, PA (US)

(73) Assignee: Arrow International, Inc., Reading, PA (US)

( * ) Notice: Subject to any disclaimer, the term of this patent is extended or adjusted under 35 U.S.C. 154(b) by 787 days.

(21) Appl. No.: 10/441,867

(22) Filed: May 20, 2003

(65) Prior Publication Data

US 2004/0049231 A1    Mar. 11, 2004

Related U.S. Application Data

(60) Continuation-in-part of application No. 10/188,605, filed on Jul. 2, 2002, now Pat. No. 6,973,346, which is a division of application No. 09/524,467, filed on Mar. 13, 2000, now Pat. No. 6,456,874.

(51) Int. Cl.
*A61N 1/18* (2006.01)
(52) U.S. Cl. .......................................... 607/3
(58) Field of Classification Search ............. 607/3, 607/43, 46, 48, 115–117; 606/129; 600/554, 600/585, 548; 604/20, 117
See application file for complete search history.

(56) References Cited

U.S. PATENT DOCUMENTS 2,987,292 A     6/1961   Teson et al.

(Continued)

FOREIGN PATENT DOCUMENTS

DE    3102142 A1    8/1982

(Continued)

OTHER PUBLICATIONS

Boezaart et al., "A new technique of continuous interscalene nerve block," Canadian Journal of Anesthesia, Mar. 1999, pp. 275-281, vol. 46, No. 3, Canadian Anesthesiologists' Society Canada.

(Continued)

*Primary Examiner*—George Manuel
(74) *Attorney, Agent, or Firm*—Amster, Rothstein & Ebenstein LLP

(57) ABSTRACT

A needle and catheter system, including components, is provided such that the position of an stimulating needle may be identified after insertion into the body of a patient by electrically stimulating and thus locating a specific nerve. Positioning of the stimulating needle while simultaneously controlling and monitoring the electrical impulses applied therethrough is made possible by a control device and monitor integral with the stimulating needle. When a specific nerve is located, the catheter is inserted through the needle to a point slightly beyond the distal tip of the needle. The catheter tip may then be manipulated and the optimum position for the catheter tip determined by applying an electrical impulse through the helical wire and/or the ribbon support wire to the proximal tip catheter, this electrical stimulation being utilized in determining the specific location of the catheter tip within the nerve. Once properly located, or at any time relative movement between the catheter and needle is not desirable, the catheter can be locked into position with a catheter lock which may be part of the stimulating needle hub. A catheter adapter is utilized to allow easy access to the catheter and introduction of fluid into the nerve of the patient through the catheter tip.

42 Claims, 16 Drawing Sheets

U.S. PATENT DOCUMENTS

| | | |
|---|---|---|
| 3,550,861 A | 12/1970 | Teson |
| 3,682,162 A | 8/1972 | Colyer |
| 4,515,168 A | 5/1985 | Chester et al. |
| 4,518,383 A | 5/1985 | Evans |
| 4,540,411 A | 9/1985 | Bodicky |
| 4,644,960 A | 2/1987 | Johans |
| 4,801,293 A | 1/1989 | Jackson |
| 4,824,433 A | 4/1989 | Marz et al. |
| 4,973,312 A | 11/1990 | Andrew |
| 5,007,902 A | 4/1991 | Witt |
| 5,081,990 A | 1/1992 | Deletis |
| 5,092,344 A | 3/1992 | Lee |
| 5,135,525 A | 8/1992 | Biscoping et al. |
| 5,284,153 A | 2/1994 | Raymond et al. |
| 5,304,141 A | 4/1994 | Johnson et al. |
| 5,423,877 A | 6/1995 | Mackey |
| 5,489,274 A | 2/1996 | Chu et al. |
| 5,782,505 A | 7/1998 | Brooks et al. |
| 5,830,151 A | 11/1998 | Hadzic et al. |
| 5,899,891 A | 5/1999 | Racz |
| 5,902,273 A | 5/1999 | Yang et al. |
| 5,976,110 A | 11/1999 | Greengrass et al. |
| 5,989,223 A | 11/1999 | Chu et al. |
| 6,104,960 A | 8/2000 | Duysens et al. |
| 6,190,370 B1 | 2/2001 | Tsui |
| 6,259,945 B1 | 7/2001 | Epstein et al. |
| 6,298,256 B1 | 10/2001 | Meyer |
| 6,325,764 B1 | 12/2001 | Griffith et al. |
| 6,582,441 B1 * | 6/2003 | He et al. .................. 606/129 |
| 6,706,016 B2 | 3/2004 | Cory et al. |
| 6,730,083 B2 | 5/2004 | Freigang et al. |
| 2002/0065481 A1 | 5/2002 | Cory et al. |
| 2003/0158592 A1 | 8/2003 | Pajunk et al. |

FOREIGN PATENT DOCUMENTS

| | | |
|---|---|---|
| EP | 0759307 A2 | 2/1997 |
| EP | 0966922 | 12/1999 |
| WO | WO 9314710 A | 8/1993 |
| WO | WO 9833547 | 8/1998 |
| WO | WO 9904705 | 2/1999 |

OTHER PUBLICATIONS

Sarnoff, S.J. and Sarnoff, L.C.: Prolonged Peripheral Nerve Block by Means of Indwelling Plastic Catheter Treatment of Hiccup. Dated 1950.

Sarnoff, S.J.: Functional Localization of Interspinal Catheters, Anesthesiology 11:300-866 (May) 1950.

* cited by examiner

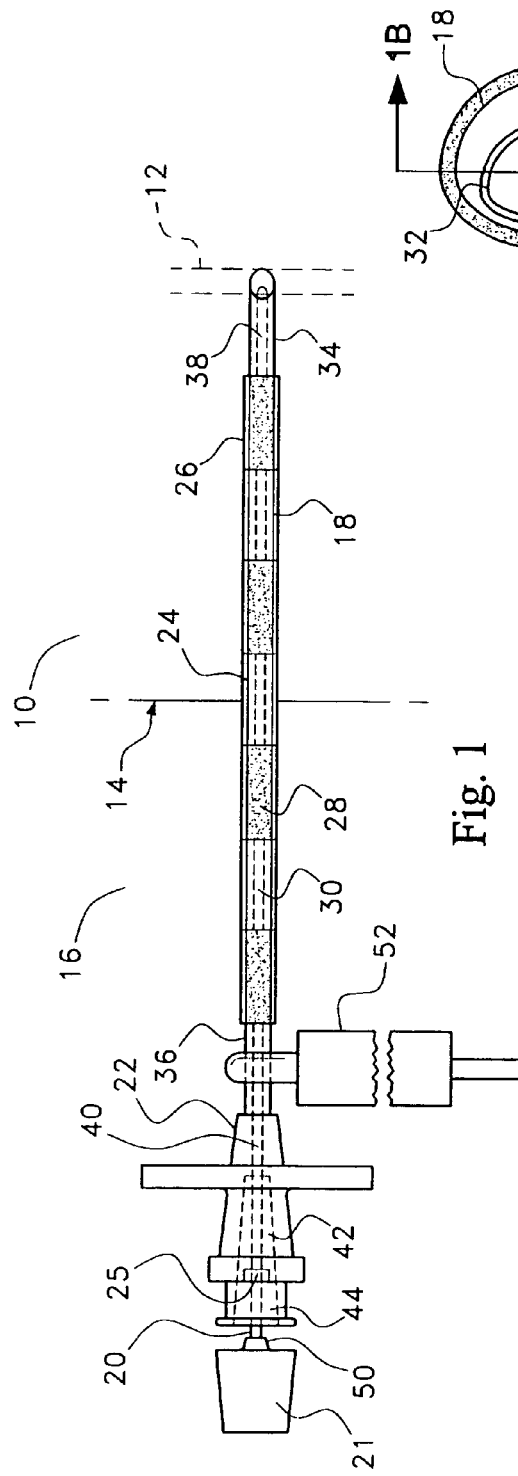
Fig. 1A
Fig. 1
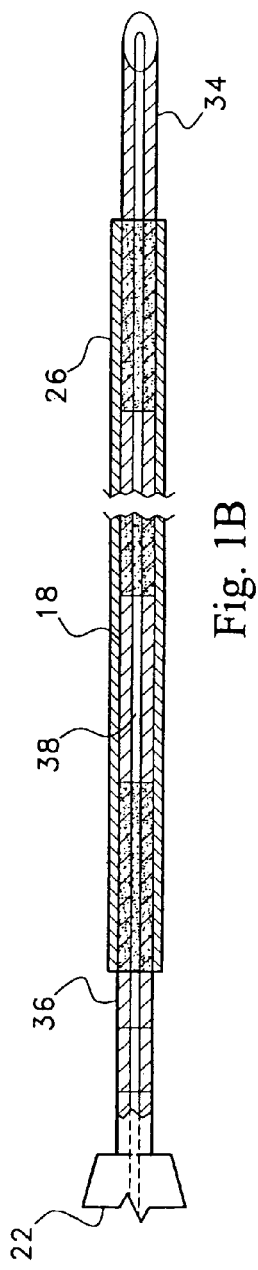
Fig. 1B

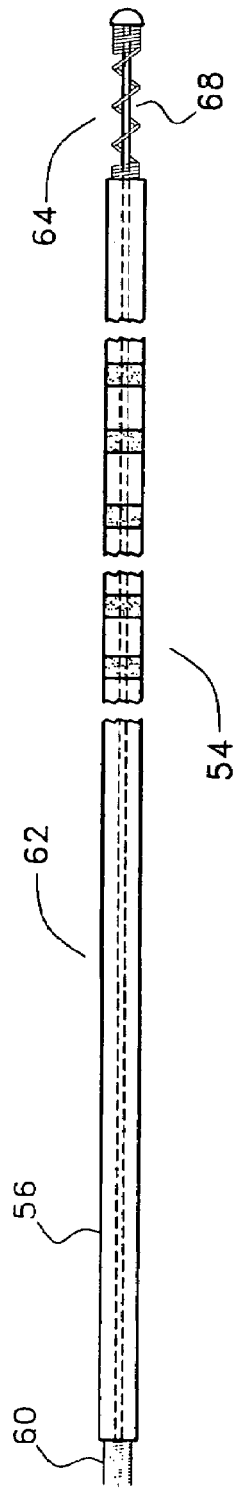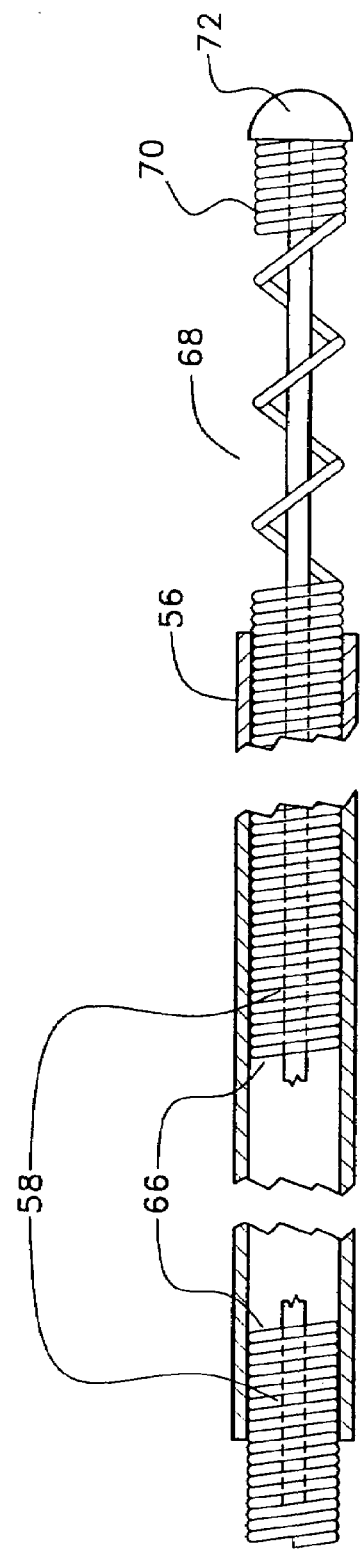
Fig. 2
Fig. 3

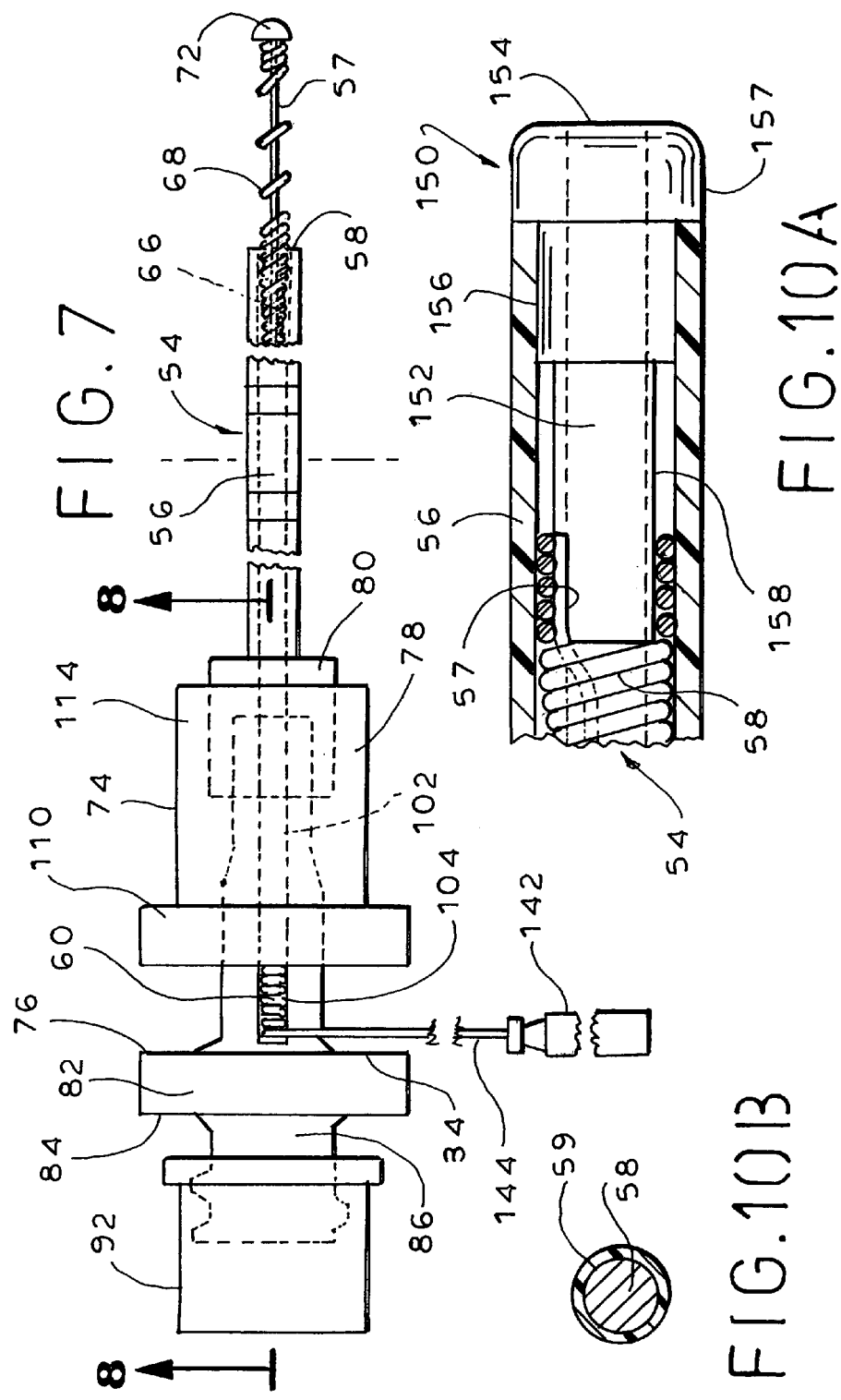

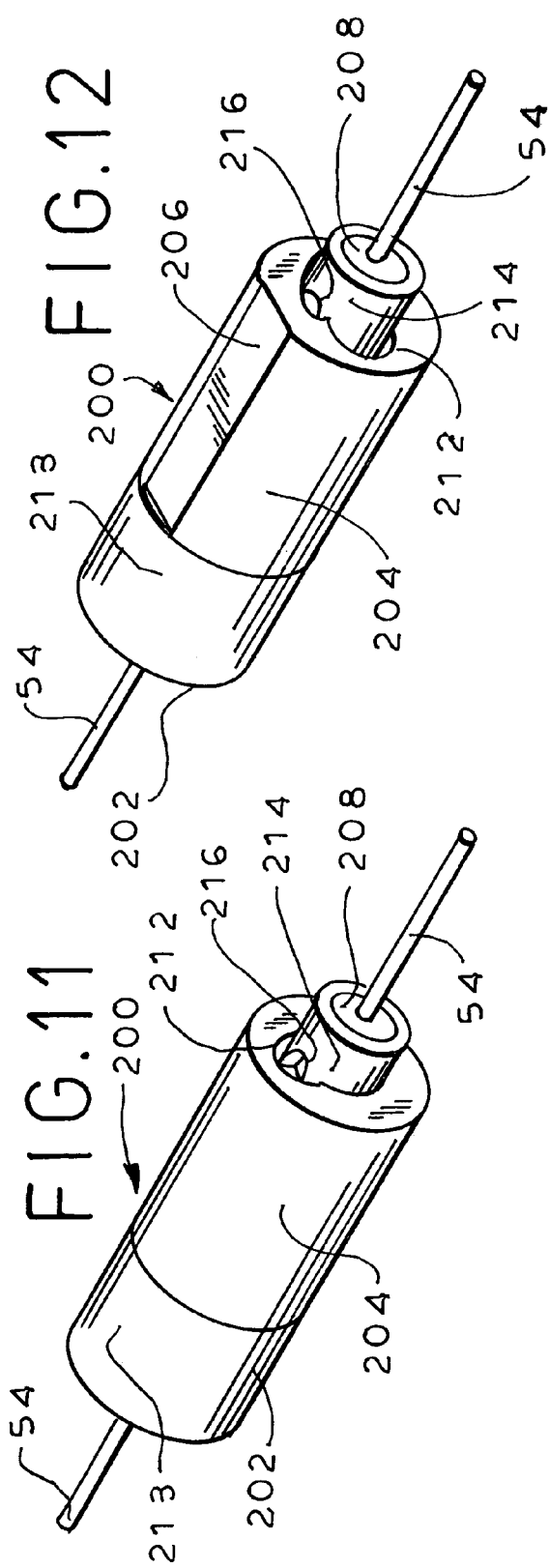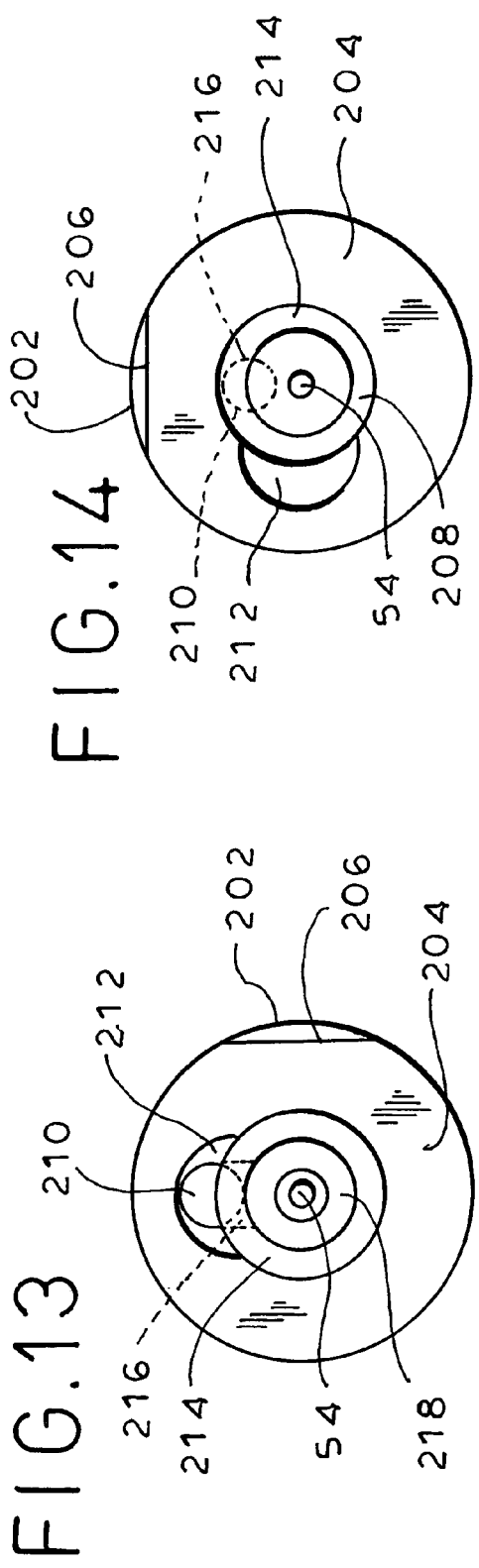

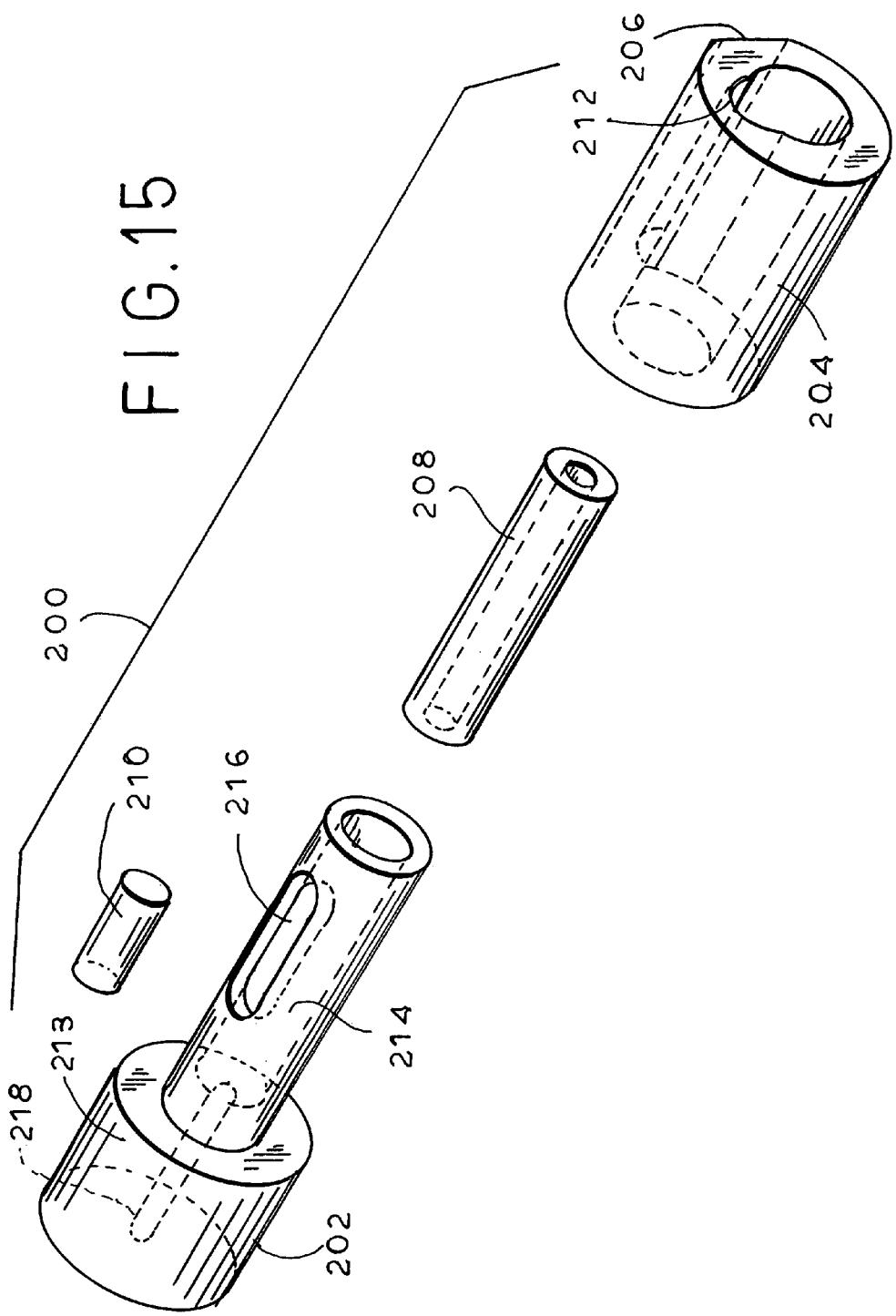

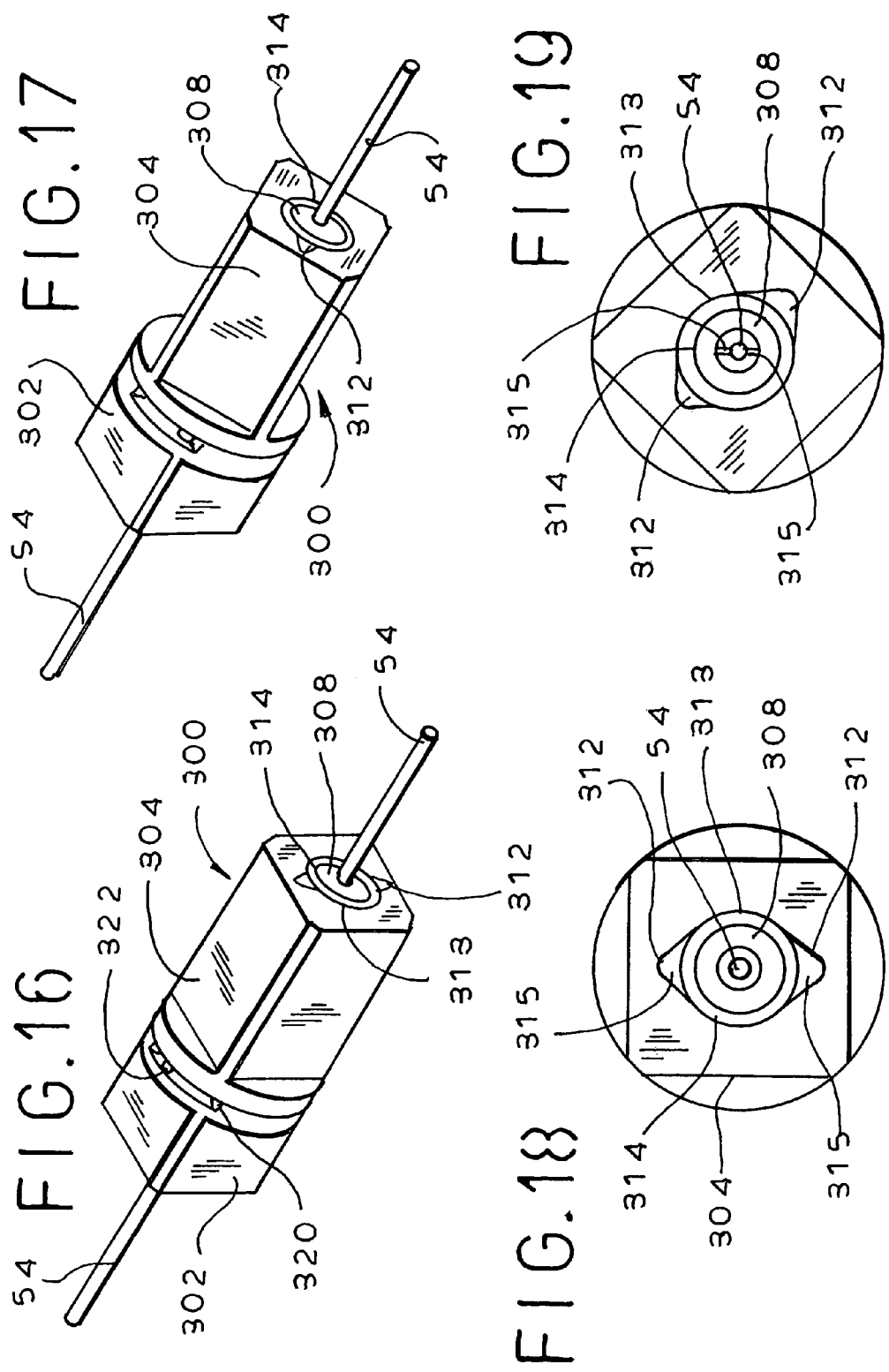

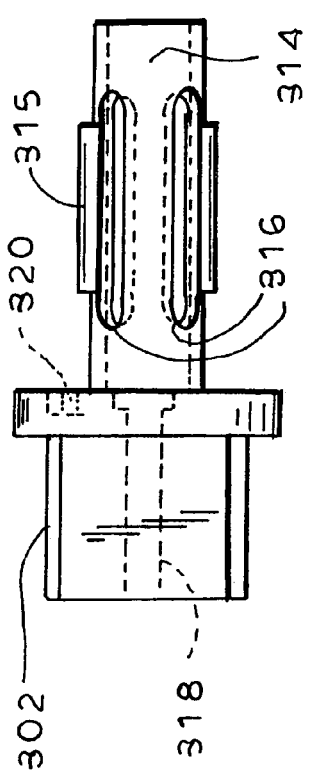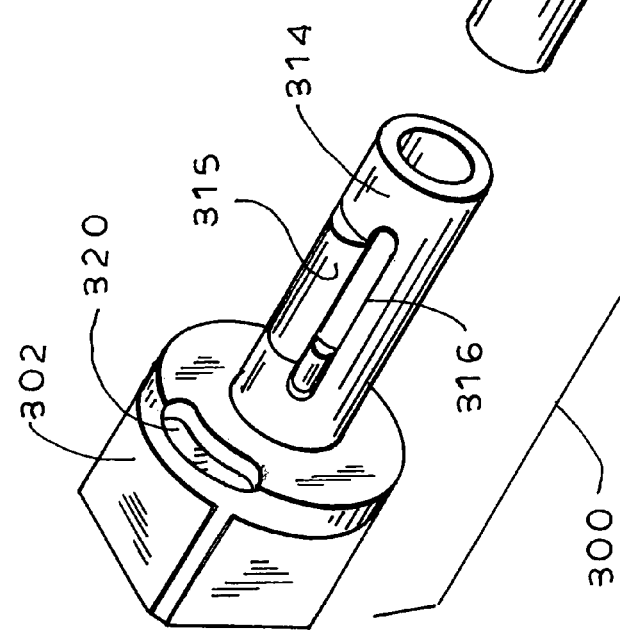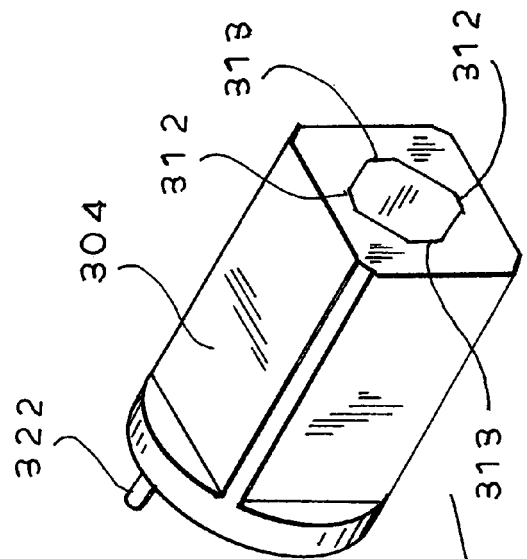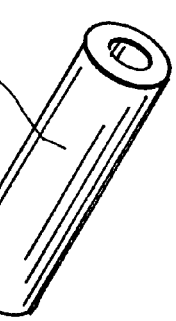
FIG. 21
FIG. 20

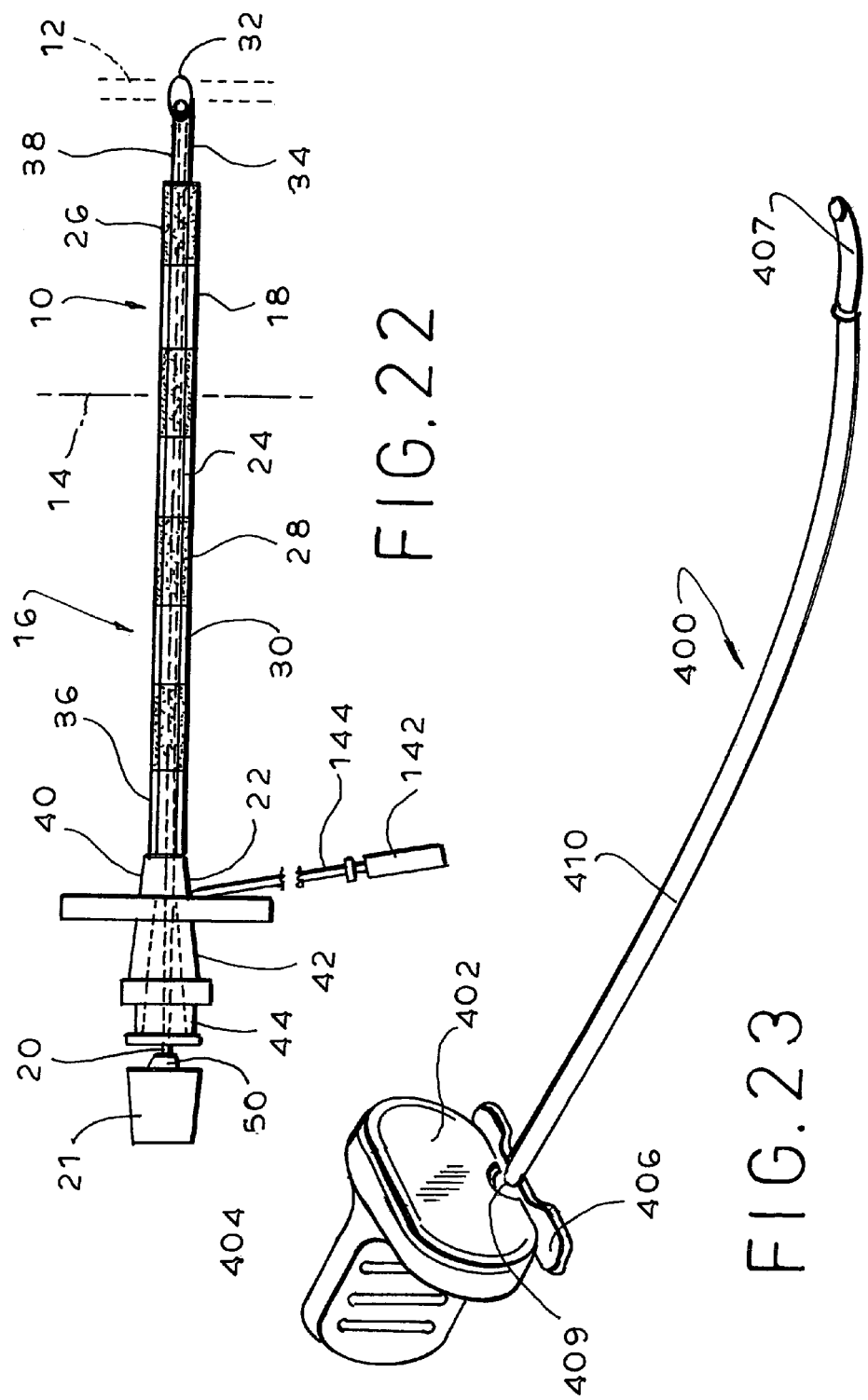

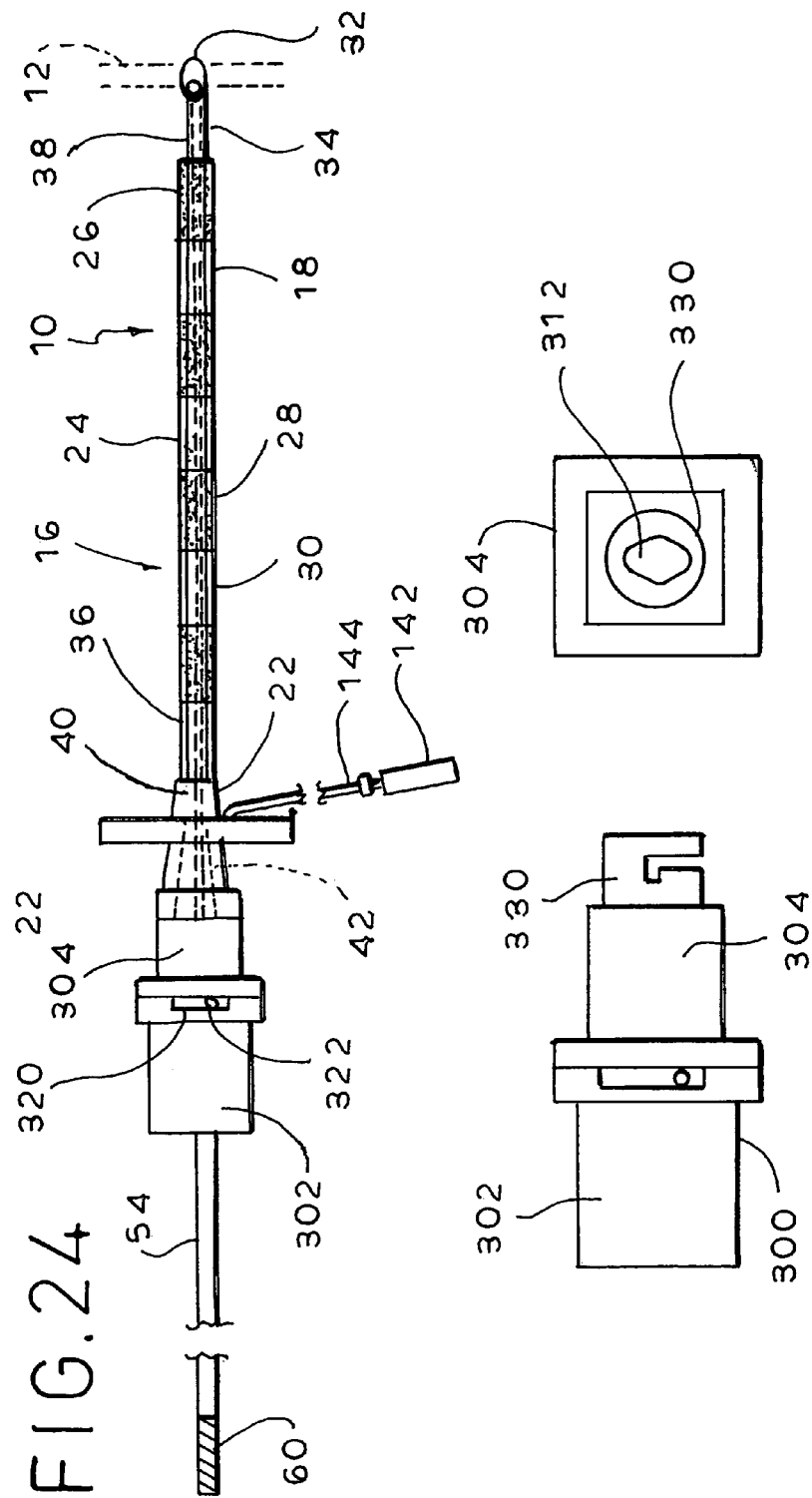

INSTRUMENT AND METHOD FOR DELIVERY OF ANAESTHETIC DRUGS

CROSS REFERENCE TO RELATED APPLICATION

This application is a continuation-in-part application of prior U.S. patent application Ser. No. 10/188,605, filed on Jul. 2, 2002 now U.S. Pat. No. 6,973,346, which is itself a divisional of U.S. patent application Ser. No. 09/524,467 entitled INSTRUMENT AND METHOD FOR DELIVERY OF ANAESTHETIC DRUG filed on Mar. 13, 2000, now U.S. Pat. No. 6,456,874.

BACKGROUND OF THE INVENTION

This invention relates to medical surgical instruments and a method of utilizing medical-surgical instruments for delivery of an anaesthetic drug. The invention is more particularly concerned with instruments and methods for use in the delivery of an anaesthetic for use as a nerve block.

A nerve block may be achieved through the administration of variable quantities of an anaesthetic agent to the plexus of a nerve. Since the nerve plexus is a very fragile structure, not capable of simple repair or reconstruction, it is crucial to do as little damage as possible in locating the point at which the plexus may be contacted.

It has been proposed to use a needle to locate the nerve in the usual way, and then to insert anaesthetic through the needle so that it emerges from the tip of the needle and contacts the nerve. An alternative procedure involves the proper positioning of the needle and the introduction of a stimulating catheter through the needle. Once properly placed adjacent the nerve and into the plexus sheath of the patient, the stimulating catheter may then be used to deliver variable amounts of anaesthetic for use as a nerve block.

It has also been proposed that an integral conductive wire be contained in the catheter, through which an electrical current may be applied to determine correct positioning of the catheter once it has been inserted through the needle. An electrical impulse sent through the conductive wire is utilized in determining proper placement of the tip of the catheter and, thus, the point at which the anaesthetic will be delivered.

Certain disadvantages exist with regard to the above referenced methods and the apparatus available to accomplish such methods. Most important among these is a danger associated with the uncertainty regarding the position of the needle tip. Such uncertainty could lead to nerve damage in manipulating the tip of the needle without knowing its position relative to nerves in the patient's body. This uncertainty can be related to 'leakage' of electricity from the needle, i.e. the electricity being applied to the needle is not exiting the needle at the tip but rather it is exiting at an unintended portion of the needle. Placement of the catheter can have similar difficulties. The catheter itself can also be unwieldy as it is usually of a very small diameter and needs to be packaged in a wound position.

BRIEF SUMMARY OF THE INVENTION

In accordance with the present invention, a catheter system is provided comprising: (a) a needle; (b) a catheter; and (c) a multipurpose connector. Each of these structures may be provided with a conductive element capable of allowing electrical contact to any other structure.

The needle has a distal end and a proximal end. The distal end of the needle terminates in a beveled aperture having a sharp tip adapted for insertion into a nerve sheath of a patient so as to abut the nerve plexus. Contained in the needle and co-terminus therewith at the distal end is a removable stylet utilized in easing insertion of the needle into the patient. The proximal end of the needle is provided with a hub portion used for gripping the needle as well as for accessing the central bore of the needle. The needle, being of metal construction, is electrically conductive along its entire length. A non-conductive material may be used to coat the outer surface of the needle, leaving exposed at least the distal tip of the needle, such that electrical voltage is not expended in unnecessary places.

A control device may be associated with the stimulating needle. The control device allows the operator to exercise control over the electrical stimulating pulse being applied to the nerve of the patient without removing either hand from the stimulating needle. Associating the control device directly with the stimulating needle has many advantages, including allowing the person inserting the needle to concentrate all of his attention on the patient and the stimulating needle without the need to operate or direct the operation of a separate, i.e. remote, stimulating control apparatus. In addition, a display may also be associated with the stimulating catheter. Such a readout would provide the operator with information as to the electrical impulse being applied to the patient's nerve. Again, the ability to focus on the single needle structure instead of referencing an independent readout remote from the stimulating needle allows for effective and safe operation of the stimulating needle and/or the stimulating catheter.

The stimulating catheter is adapted for insertion through the hub portion and within and through the needle, with the distal end of the catheter capable of protruding out of the needle's distal end. The catheter is formed primarily of a thermoplastic or related material which may be supported by a tightly wound helical wire. The helical wire can extend beyond the sheath material of the catheter at either or both the proximal and distal ends of the sheath. The sheath either alone or in combination with the helix formed by the helical wire, leaves the center of the catheter structure available as a conduit. This central conduit or lumen of the catheter allows for administration of anaesthetic to the proximal end of the catheter. The wire coil may be covered with an insulating material other than the thermoplastic cover. This insulating material, e.g. TEFLON, may surround the entire circumference of the wire as it is formed, prior to being coiled. Alternatively, this insulating material may be applied to the wire after it has been formed into a helical shape. In either case, the insulating material is typically much thinner than the thermoplastic cover applied after coiling of the wire.

The proximal end of the catheter may be inserted into a multipurpose connector. Once the proximal end of the catheter is inserted into the retaining portion of the multipurpose connector, the multipurpose connector may be manipulated to rigidly capture the proximal end of the catheter. The structure of the multipurpose connector allows the proximal end of the catheter to be accessed by a syringe or other apparatus for injecting fluid through the catheter. The multipurpose connector is also provided with electrical connections which electrically contact the helical wire of the catheter or other electrically conducting portions of the catheter. These electrical contacts allow a voltage to be applied to a conducting portion of the catheter despite the presence of the multipurpose connector over the proximal end of the catheter.

Another component that may be used in conjunction with the stimulating needle and the catheter system is a catheter lock. The catheter lock fits over the catheter and allows the catheter to slide therethrough when 'unlocked'. When actuated, i.e. 'locked', the catheter lock firmly grips whatever portion of the catheter it is on when actuated. This gripping function may be used to securely hold the catheter especially when it is desired that the catheter be maintained in a given position. One of the ways in which the catheter lock can be used is in conjunction with the stimulating needle. Attachment of the catheter lock to the proximal end of the gripping hub of the stimulating needle allows for the catheter to be manipulated with respect to the stimulating needle or rigidly fixed in place with respect to the stimulating needle.

It is therefore an object of the present invention to provide a stimulating needle and stimulating catheter system including components, such that the position of a needle may be identified by electrically stimulating and thus locating a specific nerve. When a specific nerve is located, the stimulating catheter is inserted through the needle to a point slightly beyond the distal tip of the needle. The catheter tip may then be manipulated and the optimum position for the catheter tip determined by applying an electrical voltage to the conducting distal tip of the catheter, this electrical stimulation being utilized in locating the specific location of the catheter tip with respect to the nerve. Once optimum placement is achieved, the catheter is utilized for continuous administration of anaesthetic. At any time prior to this positioning procedure, when it is desired to hold the catheter in a particular place, actuation of a catheter lock structure allows this to be accomplished. In addition, once desired placement of the catheter is achieved, the stimulating needle may be removed in order to prevent it from doing any damage to the tissues of the patient.

It is a further object of the present invention to allow the person using the system to be able to easily vary the current being applied to the patient's nerve. Such a varying of the electrical impulses would be achieved without having to divert the operator's attention away from the apparatus being inserted into the patient. Also, a readout allows the operator to monitor the electrical impulses being applied to the nerve of a patient. The readout, too, is associated with the needle and allows monitoring of the electrical stimulation signal with a minimum of distraction from the insertion of the apparatus.

Some of the objects of the invention having been stated above, other objects will become evident as the description proceeds below, when taken in connection with the accompanying drawings as best described below.

BRIEF DESCRIPTION OF THE DRAWINGS

FIG. 1 is a side elevational view of the needle and stylet, with the needle inserted into the nerve sheath;

FIG. 1A is an end-on elevational view from the distal end of the needle structure, showing a detail of the tip of the needle, the tip of the stylet the and non-conductive needle material covering the region of the needle between the proximal ends;

FIG. 1B is a top view of the needle, with only a portion of the hub shown and the stylet removed, most of the needle being shown in section at section line 1B-1B;

FIG. 2 is a side elevational view of the catheter;

FIG. 3 is an enlarged version of FIG. 2, except that the catheter sheath is partially cut away to better show the structure of the helical wire, only portions of which are shown;

FIG. 7 is a side elevational view of an alternate embodiment of the multipurpose connector, with the proximal end of the catheter inserted therein but not yet rigidly held in place and the distal end of the catheter also shown with much of the intervening catheter cut away;

FIG. 10A is an side elevational detail of the slug type distal tip shown inserted into the distal end of an alternate version of the catheter, the catheter is in section;

FIG. 10B is cross sectional detail view of the helical support wire of the catheter showing the electrically insulating coating disposed thereon as discussed in reference to an alternate embodiment;

FIG. 11 is a perspective view of a first embodiment of a catheter lock shown in the unlocked position;

FIG. 12 is a perspective view of the first embodiment of the catheter lock shown in the locked position;

FIG. 13 is an end-on view of the first embodiment of catheter lock shown in the unlocked position;

FIG. 14 is an end-on view of the first embodiment of catheter lock shown in the locked position;

FIG. 15 is an exploded detail view the first embodiment of the catheter lock showing each of the components thereof;

FIG. 16 is a perspective view of a second embodiment of a catheter lock shown in the unlocked position;

FIG. 17 is a perspective view of the second embodiment of the catheter lock shown in the locked position;

FIG. 18 is an end-on view of the second embodiment of the catheter lock shown in the unlocked position;

FIG. 19 is an end-on view of the second embodiment of the catheter lock shown in the locked position;

FIG. 20 is an exploded detail view the second embodiment of the catheter lock showing each of the components thereof;

FIG. 21 is a side elevational view of the stationary body portion of the second embodiment of the catheter lock including the cylindrical extension portion thereof;

FIG. 22 is a side elevational view of the needle and stylet, with the needle inserted into the nerve sheath;

FIG. 23 is a perspective view of a tunneling device with integral gripping hub and skin bridge;

FIG. 24 is a side elevational view of the needle, needle hub and catheter lock extending proximally therefrom;

FIG. 25A is a side elevational view of one embodiment of the catheter lock according to the present invention;

FIG. 25B is an end view of one embodiment of the catheter lock according to the present invention;

DETAILED DESCRIPTION OF THE INVENTION

Figure 1D:
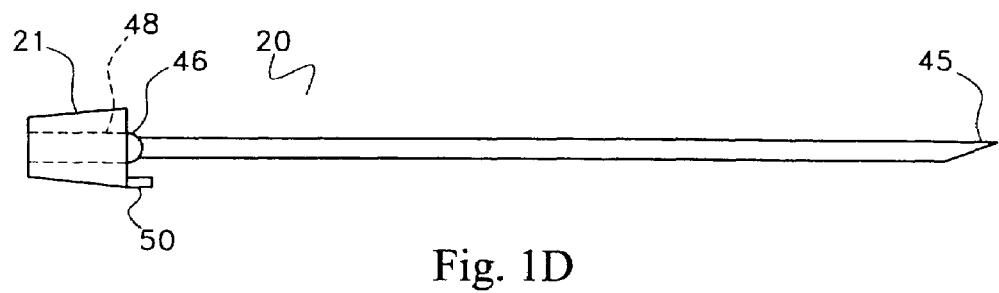
FIG. 1D is a side elevational view of the inner stylet.

Referring first to FIG. 1, there is shown portions of a human body 10 containing a nerve 12 located subcutaneous to adjacent skin surface portion 14. In this example of use, a needle assembly 16 has been inserted into a human body 10 for the purpose of locating a nerve 12. The stimulating needle assembly 16 comprises a needle 18 and a central stylet 20 which extend coaxially of one another. The needle 18 is a metal needle which is joined at its rear end to a hub 22 of a plastic material. The needle 18 is hollow and projects a distance forwardly of the hub 22.

The needle 18 has three portions along its length. The major portion of the needle is the central portion 24 thereof. This central portion 24 of the needle is wrapped on the outside surface thereof in an insulating coating 26 which will not conduct electricity. This coating 26 is shown in FIG. 1 as being divided into sections of alternating color 28 and 30. Each of these sections is of a known, specific, length. Such colored sectioning enables the user to determine the extent of penetration of the tip 32 of the needle 18. Alternatively, the coating 26 may be clear and the underlying surface of the needle 18 may be marked, e.g. with alternating colors or other depth markings.

The remaining two portions of the needle 18 are the distal end 34 and the proximal end 36. At its proximal end 36, the needle 18 extends within the hub 22 where it is secured, such as by molding the hub around the needle. Between the insulating coating 26 of the central portion of the needle 24 and the plastic hub 22 the proximal end 36 of the needle 18 may be exposed such that electrical contact with the remainder of the needle may be achieved by contact with the exposed proximal end 36. The bore through the needle 38 opens into an axially-aligned bore 40 through the hub 22 of the same diameter as the needle bore 38. The rear end of the bore 42 is enlarged and tapered to provide a female Luer opening 44 for use in receiving the stylet 20 and stylet hub 21. The hub 22 is provided with an axially-extending slot or keyway 25 formed in the outer surface of the hub, on that side of the hub to which the tip 32 of the needle 18 is inclined.

Figure 1C:
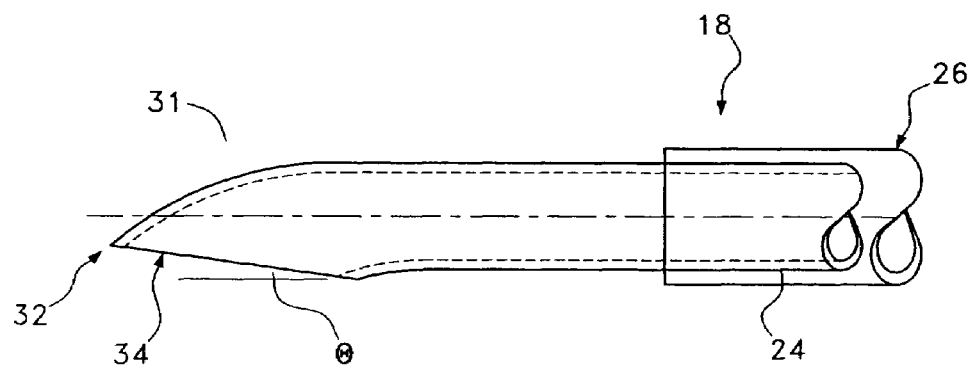
FIG. 1C is a detail of the needle tip.

As shown in FIG. 1C, the distal end 31 of the needle 18 is bent downwardly, the distal end 34 of the needle being cut such that it makes an angle θ with the axis of the major part of the needle. This inclined end of the needle provides it with a tip 32 constituting a sharp point that readily pierces body tissue. In this embodiment, the distal end 34 of the needle is not covered by any electrically insulating material and is in electrical contact, by way of the covered central portion 24, with the proximal end 36 of the needle. The insulating coating 26 prevents the flow of electricity radially out of the central portion 24 of the needle, but allows the flow of electricity axially along the length of the needle 18.

As best exemplified in FIG. 1D, the inner stylet 20 is formed of a solid metal needle. The distal tip 45 of the stylet 20 is cut to have the same sharp tip angle θ as the tip 32 of the needle. Joined to the proximal end of the stylet 20 is a stylet hub 21 of plastic material. The stylet 20 is smaller in diameter than the outer needle 18. The connector 46 of the stylet hub 21 which grasps the stylet 20 is of generally cylindrical shape. The forward end of the connector 46 has a Luer taper 48 that is dimensioned to fit within the Luer-tapered opening 44 in the needle hub 22. A short peg or key 50 of rectangular section is provided along the lower side of the stylet hub 21, as viewed in FIG. 1. The peg 50 extends axially of the stylet hub 21, being spaced outwardly by a small gap from its Luer-tapered section 48. The peg 50 is aligned with respect to the stylet hub 21 and stylet 20 such that, when the peg is engaged in the slot 25 of the needle hub 22, the plane of the inclined tip 45 of the stylet 20 lies in the same plane as the inclined tip 34 of the needle. The combined sharp tips of the needle and stylet readily pierces body tissue while the stylet, occupying the center bore 38 of the needle, prevents any tissue from entering the needle bore 38.

Also shown in FIG. 1 is an electrical connector 52, which may be in the form of an alligator clip which conveys electrical impulses from an anaesthetic nerve stimulator 17 to the proximal end of the needle 36.

FIG. 1A is an end on view of the tip of the needle assembly 16, showing the inclined tip of the needle 32 and the inclined tip 45 of the stylet 20. Also shown is the insulating coating 26. FIG. 1B is a detail of the needle 18 of the needle assembly, with the stylet 20 removed and only showing a small portion of the hub 22. In addition, the needle 18 of FIG. 1 has been sectioned along section line 1B of FIG. 1A. FIG. 1B shows the relationship of the insulating coating 26 (of exaggerated thickness) to the various portions of the needle 18.

Referring next to FIG. 2, there is shown a catheter assembly 54. The catheter assembly 54 is of a diameter which allows the assembly to be inserted through the needle assembly 16 and into the body of the patient. The catheter assembly 54 is primarily defined by a sheath 56 formed from a thermoplastic or similar material. A helical coil of wire 58 may also be utilized in conjunction with catheter sheath 56. As best shown in FIG. 3, helical wire 58 possesses three portions. A proximal portion 60, a central portion 62 and a distal portion 64. For its entire length, catheter assembly 54 defines a central bore 66 through which a liquid may freely pass. In addition, the helical wire 58 occupies only the peripheral portion of the central bore 66, thus maintaining the presence of central bore 66. This central bore 66 can also be seen to be extended beyond the catheter sheath by the presence of the helical wire 58. The helical wire 58 is not a necessary element of the catheter assembly 54. Rather, the helical wire can be eliminated, especially where the catheter is of sufficient strength so as to support itself.

Also occupying the central bore 66 of the catheter assembly 54 is ribbon wire 57. Ribbon wire 57 has two primary functions. The first of these functions is to prevent wire helix 58, if present, from being hyperextended. This function is accomplished by rigidly attaching ribbon wire 57 to distal tip 72, discussed more fully below, and to the proximal portion 60 of the helical wire 58. Attachment of the ribbon wire 57 at these portions of the helical wire will prevent the helix from being stretched in such a way as to permanently deform the wire. The second function of the ribbon wire 57 is to conduct electricity from the proximal portion of the catheter to the distal tip 72 of the catheter. This conduction of electricity may be supplemental to the electrical conduction of the wire helix 58 or it may be as an alternative to the electrical conduction provided by the wire helix. This interchangeability is obvious, given the fact that the wire helix 58 and the ribbon wire 57 both extend from the proximal end of the catheter to the distal tip 72. Thus, the wire helix 58 and the ribbon wire 57 are alternatives for conducting an electrical impulse from one end of the catheter assembly 54 to the other. If one of these two wires is present to accomplish this, there is no need for the other one.

The central portion 62 of the helical wire 58 is completely covered by the catheter sheath 56. The proximal portion 60 of the helical wire has no distinguishing features except that it is short relative to the central portion of the remainder of the catheter assembly 54 and is not covered by the catheter sheath. Proximal portion 60 of helical wire 58 can be electrically contacted. This can be accomplished by leaving it exposed as in FIG. 2 or by providing an electrical contact such as a wire, as will be discussed below.

In an alternate embodiment of the apparatus, the wire coil may be covered with an insulating material 59 other than or in addition to the thermoplastic cover provided by the catheter sheath 56. This additional insulating material 59, e.g. PTFE (Polytetrafluoroethylene) "TEFLON", surrounds the entire circumference of the wire as it is formed, prior to being coiled. Alternatively, the thin insulating coating 59 can be applied after the wire is formed into a helical coil. Such an insulating material 59 is typically much thinner than the thermoplastic cover applied to the entire coil after the wire coil is formed. In addition, such an insulating material 59 is typically directly bonded to the surface of the wire. By coating the wire helix 58 and other portions of the present apparatus which are electrically conducting and may come in contact with the tissues of a patient with an insulating material it becomes possible to very precisely control the size and location of the conducting portions of the apparatus. This control is accomplished by removing the thin insulating material 59 only from the precise portions of the apparatus which are to deliver electrical impulses to the tissues of a patient. In addition, with only the relatively small portion of the conducting portions of the apparatus exposed, the voltage density achieved at that point is high relative to the power of the electrical impulse supplied.

The distal portion 64 of the helical wire, which is short relative to the remainder of the catheter assembly 54 and not covered by the catheter sheath 56, has several features associated therewith. Where the helical wire 58 exits the catheter sheath 56 at the distal end thereof, the helix maintains the tightly wound nature of the proximal 60 and central 62 portions of the wire. This tight helix continues for a short distance before the helix opens up at an open helix portion 68. The open helix portion 68 continues for several revolutions of the helix, before the tightly wound structure returns for the distal end 70 of the distal portion 64. Attached to the distal end 70 is a distal tip 72 which is a piece of rounded metal. As discussed above, distal tip 72 may also or alternatively have ribbon wire 57 attached thereto. As with the helical wire 58, the distal tip is conducting and can either be completely bare of insulation or be substantially covered with thin layer 59 of insulating material, e.g. PTFE, and have a specific portion uninsulated.

An issue with some catheters of the type described herein arises due to the method in which they are packaged. Due to their length, it is necessary to coil the catheter. The natural shape of these catheters being straight and the materials of which they are made typically being quite resilient, improper removal of the catheter from the packaging may result in uncontrolled uncoiling of the catheter which, in turn, can lead to safety and sterility problems. A catheter packaging clip may be provided for retaining catheter 54 to prevent rapid uncoiling. In one embodiment, the catheter packaging clip may have a surface for gripping the clip as well as integral tunnel for retaining catheter 54 in such a way that rapid uncoiling can be prevented. In a second embodiment, a catheter packaging clip may have dual gripping portions but a tunnel similar to that of the alternate embodiment. The clip may be packaged with the catheter 54.

Figure 4:
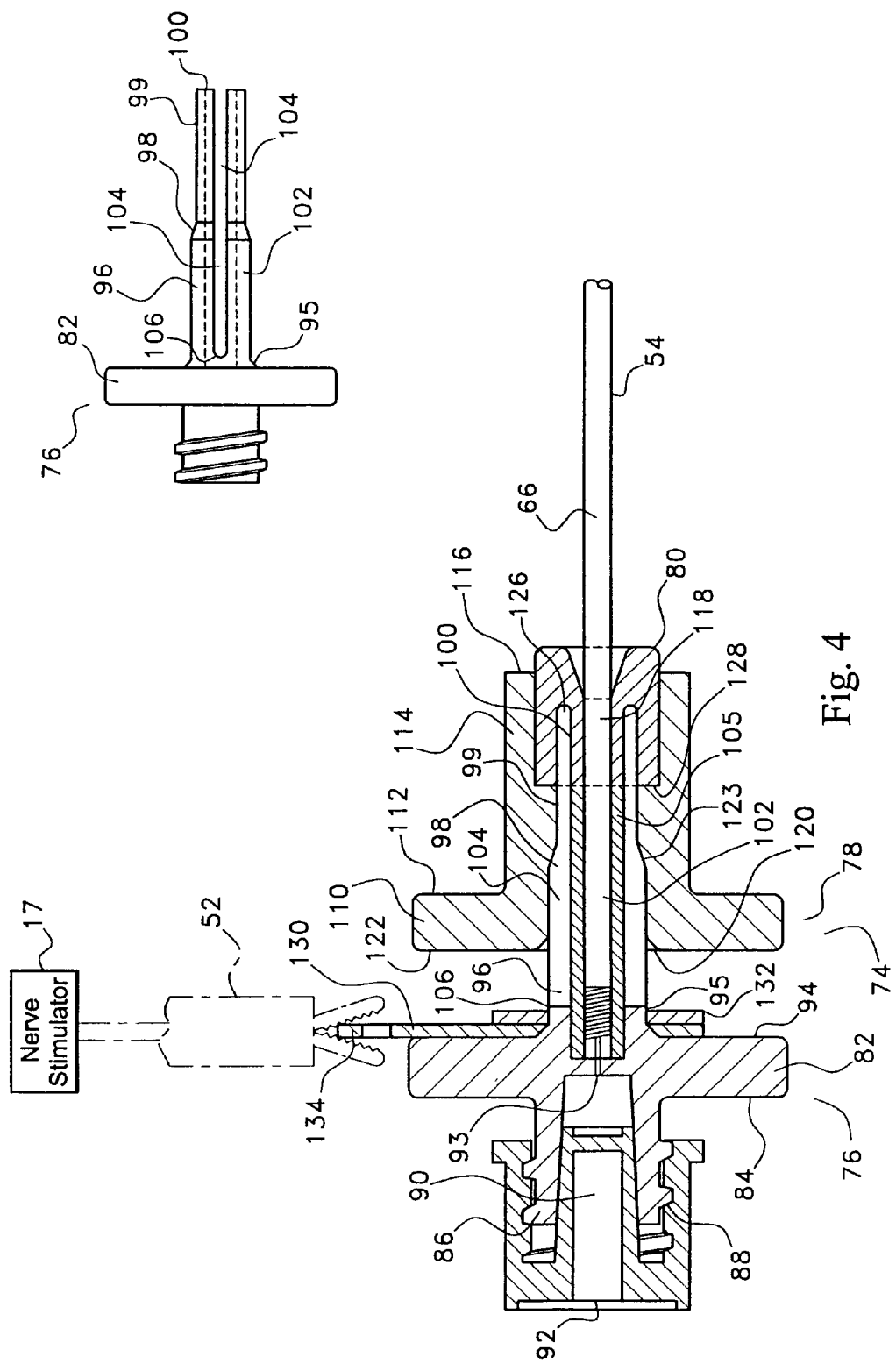
FIG. 4 is a side elevational view of the multipurpose connector in section, with the proximal end of the catheter inserted therein but not yet rigidly held in place.

Referring next to FIG. 4, there is shown a catheter adapter 74. Accessing the central bore 66 of the catheter assembly 54 would be nearly impossible given the diameter of this structure. This being the case, a catheter adapter 74 is needed to provide access to the central bore 66 of the catheter assembly 54 for various delivery vehicles, e.g. a syringe, for the controlled delivery of fluid through the catheter.

The main constituents of the catheter adapter are the rear body 76, the front body 78 and the holding hub 80. The rear body 78 has a central flange 82. From the rear face 84 of the central flange 82 extends a connection cylinder 86 having a threaded outer surface 88 and a hollow central bore 90. The function of this cylinder is to facilitate luer attachment of apparatus for controlled delivery of fluid to the catheter assembly 54. The end cap 92 provided with the catheter adapter 74 is primarily for sterility purposes, and is simply removed after the catheter adapter 74 is attached to the catheter assembly 54. The central flange has, at its center, a bore 93 passing completely therethrough such that the rear face 84 and front face 94 are in fluid communication.

From the front face 94 of the central flange 84 extends an operating cylinder 96. Where the operating cylinder 96 is connected to the front face 94 of the central flange 84, it is of a certain diameter 95. Along the length of the operating cylinder, the diameter of the operating cylinder is reduced by a taper 98. The remainder of the operating cylinder is of this reduced diameter 99 to the distal end 100 of the operating cylinder. The operating cylinder 96 has a central bore 102 which extends along the entire length thereof. Axial slots 104 extend from the distal end 100 of the operating cylinder, nearly the length thereof, i.e. the slot ends 106 extend nearly to the juncture of the operating cylinder 96 and the front face 94 of the central flange 82. Contained in and extending most of the length of the central bore 102 of the operating cylinder 96 is an elongated rubber gasket 105.

The front body 78 of the catheter adapter has a structure similar in geometry to the central flange 84 of the rear body 76, this structure is called the rear flange 110. The rear flange 110 has extending from the front face 112 thereof a front cylinder 114. The front cylinder 114 has an essentially constant outside diameter extending from the front face 112 of the rear flange 110 to the distal end 116 of the front cylinder. A central bore 118 is provided in the front cylinder 114, extending the entire length thereof. This central bore 118 has several different diameter changes along its length. At the entry portion of the central bore 120 on the rear face 122 of the rear flange, the diameter of the bore is slightly larger that the diameter 95 of the operating cylinder 96 where it is connected to the front face 94 of the central flange 84. Along the length of the central bore 120 the inside diameter is reduced by a taper 123 which is a mirror image of taper 98 on the operating cylinder. These mirror image structures thus allow sliding contact between the outer surface of the operating cylinder 96 and the central bore 120 of the front body 78.

The holding hub 80 is a generally tubular body provided with a cylindrical recess 126 formed in the rear face 128 thereof. The distal end 100 of the operating cylinder 96 is matingly engageable with the cylindrical recess 128 of the holding hub 80 and is rigidly attached thereto. The diameter of the central bore 120 of the front body 78 is, from the front face thereof 94 to a depth less than the length of the holding hub, slightly greater than the diameter of the holding hub. The rigid connection between the holding hub 80 and the distal end 100 of the operating cylinder holds these two structures in slidable relationship with the front body 78.

In use, the catheter adapter 74 is initially in the configuration shown in FIG. 4. In this configuration the proximal end 60 of the catheter assembly 54 may be freely inserted and withdrawn from the catheter adapter. The proximal end 60 of the catheter assembly 54 may be held in place by sliding the front body 78 toward the rear body 76 of the catheter adapter. In sliding these pieces relative to each other, the taper 98 of the operating cylinder 96 will be compressed by the taper 123 of the interior of the front body. The slots 104 in the operating cylinder 96 allow this compression to occur. The compression of the operating cylinder results in the compression of the elongated rubber gasket 105. This compression of the elongated rubber gasket 105 results in the rubber gasket frictionally engaging the proximal end 60 of the catheter assembly 54 such that the catheter may not be easily removed from the catheter adapter.

Figure 6:
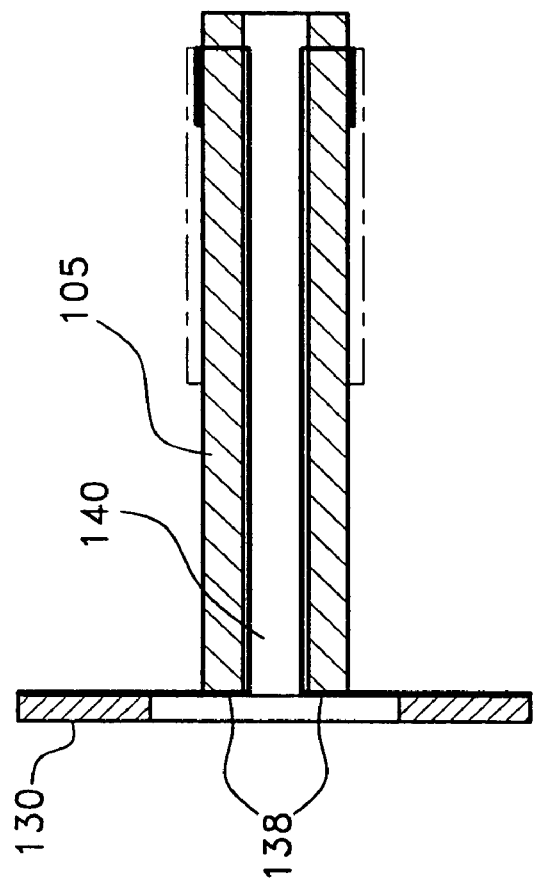
FIG. 6 is a side elevational view of the metal washer, multipurpose connector wires and sealing assembly of the multipurpose connector.
Figure 5:
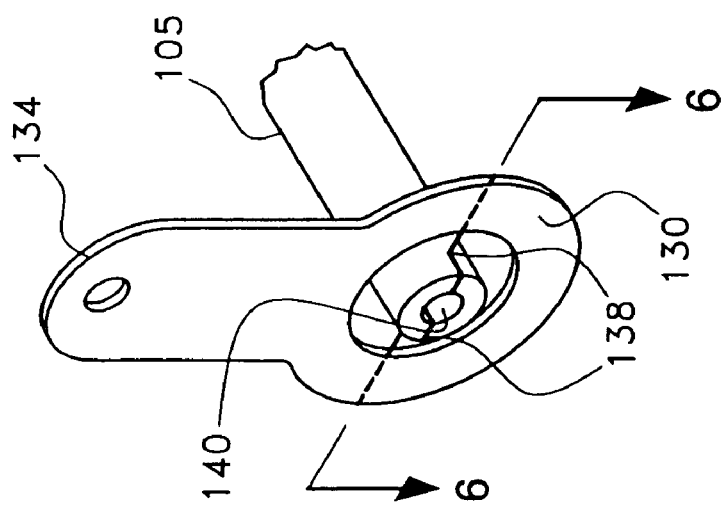
FIG. 5 is a perspective view of the metal washer, multipurpose connector wires and sealing assembly of the multipurpose connector.

An additional structure of this embodiment of the catheter adapter which is of interest is the metal washer 130. This metal washer 130 is disposed about the operating cylinder 96 adjacent the front face 94 of the central flange 82. Seal 132 prevents leakage of fluid adjacent the metal washer 130. The metal washer 130 is provided with a tab portion 134 which extends above the flange portions 84 and 110. This allows electrical contact to be made to the washer by way of the same electrical connector 52 as was used previously to conduct electricity into the needle assembly 16 from an anaesthetic nerve stimulator 17. As can be seen in FIGS. 5 and 6, a pair of wires 138 are attached to the metal washer 130 and extend from the metal washer to the internal bore 140 of the elongated rubber gasket 105. Thus, when the elongated rubber gasket 105 is compressed about the proximal end 60 of the catheter assembly 54, electrical contact is made between the pair of wires 138 and the helical wire 58. As a result, electrical contact may be made from the anaesthetic nerve stimulator 17, through the catheter adapter 74 and into the helical wire 58 of the catheter apparatus 54 and, thus, to the conductive distal tip 72 of the catheter assembly. For the embodiment where a thin layer of insulating material is disposed about the conducting portions of the assembly, removal of the insulating material at the portions which will come in contact with wires 138 is necessary. Wires 138 may also be adapted to allow electrically contact ribbon wire 57, thus allowing electrical stimulator 17 to be attachable to ribbon wire 57 through the catheter adapter 74.

In an alternate embodiment of the apparatus to be used to deliver an anaesthetic drug, several changes regarding the conduction of electricity from a voltage source, e.g. nerve stimulator 17, to the proper point inside the patient are made. This alternative embodiment allows a medical practitioner to utilize the instruments more easily, with more precision and with fewer steps as well as fewer apparatus elements to keep track of. The embodiment is described below. However, many of the elements discussed with regard to the alternate embodiment are easily interchangeable with and can be used in conjunction with other embodiments. To the extent that an element from the earlier embodiment was described above and is retained in a similar form in the following alternate embodiment, the same numbering shall be used to identify that element.

Referring first to FIG. 22, there is shown relevant portions of a human body 10 containing a nerve 12 located subcutaneous to a skin surface portion 14. A needle assembly 16 has been inserted into a specific point in the skin surface portion 14 of the human body 10 for the purpose of locating a nerve 12. The needle assembly 16 comprises a needle 18 and a central stylet 20 which extend coaxially of one another. The needle 18 is a metal needle which is joined at its rear end to a hub 22 of a plastic material. The needle 18 is hollow and projects forwardly of the hub 22.

The needle 18 has three portions along its length. The major portion of the needle is the central portion 24 thereof. This central portion 24 of the needle is wrapped on the outside surface thereof with an insulating coating 26 which will not conduct electricity. This coating 26 is shown in FIG. 22 as being divided into sections of alternating color 28 and 30. Each of these sections is of a known, specific, length. Such colored sectioning enables the user to determine the extent of penetration of the tip 32 of the needle 18.

The remaining two portions of the needle 18 are the distal end 34 and the proximal end 36. At its proximal end 36, the needle 18 extends within the hub 22 where it is secured, such as by molding the hub around the needle. In this embodiment the proximal end 36 of the needle 18 extending outside of the hub 22 is covered with insulating coating 26. The bore extending through the needle 38 opens into an axially-aligned bore 40 extending through the hub 22 having the same diameter as the needle bore 38. The rear end of the bore 40 is enlarged and tapered to provide a female Luer opening 44 for use in receiving the stylet 20 and stylet hub 21. A connection wire 144 is provided which extends through the hub 22 and is electrically connected within the hub to the needle 38. The hub 22 being an insulating material and the connection wire 144 external to the hub 22 being insulated, the leakage of voltage from the connection wire 144 is prevented. A connection plug 142 is provided on the external end of the connection wire 144. This connection plug 142 allows the connection wire 144 to be easily connected to a nerve stimulator apparatus 17.

The distal end 34 of the needle is not covered by any electrically insulating material and is in electrical contact, by way of the covered central portion 24, with the portion of the needle which is connected to the connection wire 144. The insulating coating 26 prevents the flow of electricity radially out of the central portion 24 and proximal portion 36 of the needle, but allows the flow of electricity axially along the length of the needle 18.

The inner stylet 20 is of the same construction as described with respect to FIGS. 1 and 1D.

Figure 9:
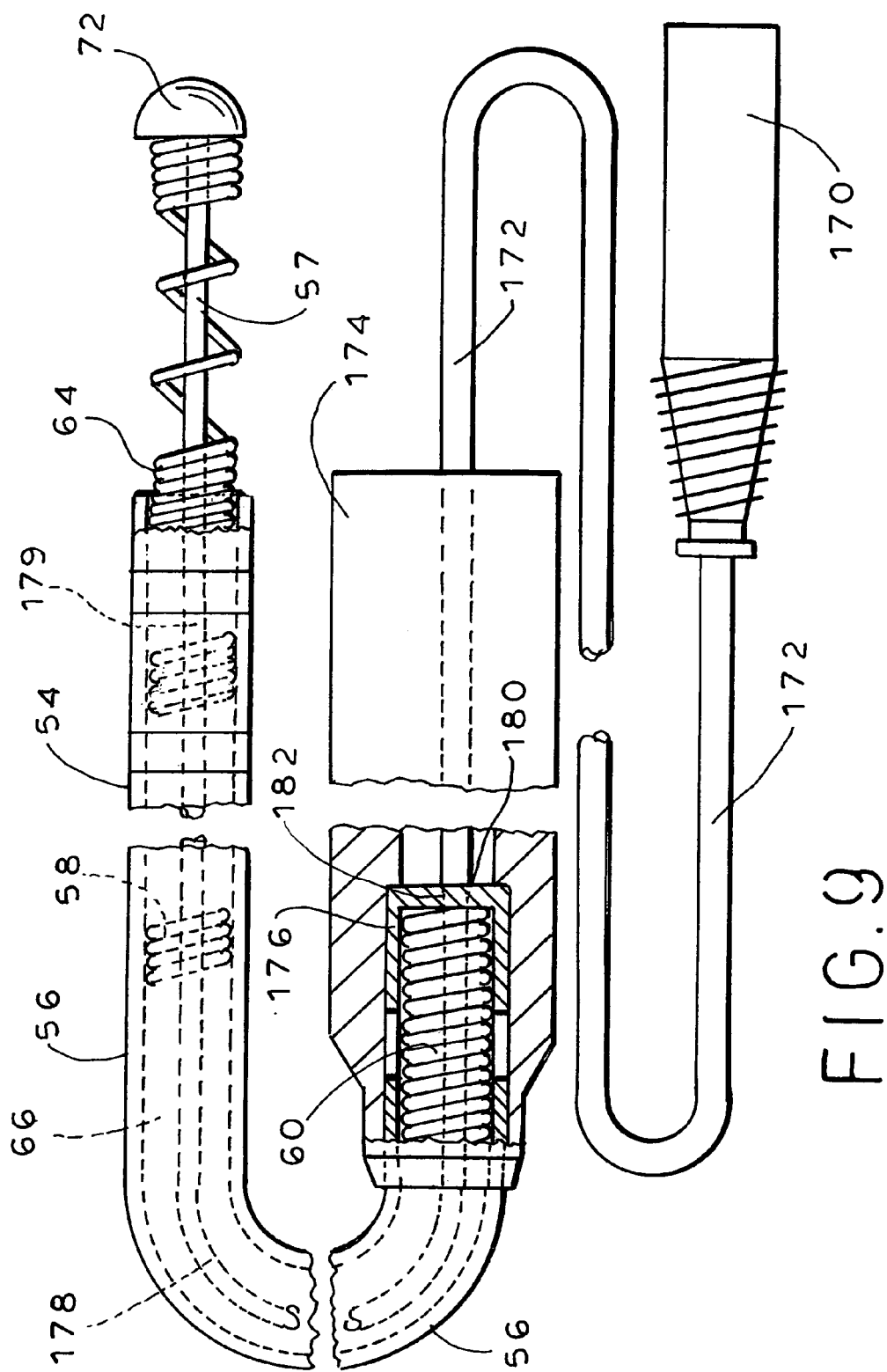
FIG. 9 is a side elevational view of the catheter disclosing some inner structures therein in partial cross-section, an electrical connection hub and an electrical connection plug.

Referring next to FIG. 9, there is shown a catheter assembly 54 in combination with other elements of this embodiment. The catheter assembly 54 is essentially the same as described previously and of a diameter which allows the assembly to be inserted through the needle assembly 16 and into the body of the patient. The catheter comprises a sheath 56 formed from a thermoplastic or similar material. The helical wire 58 and sheath 56 define a central bore 66 through which a liquid may freely pass.

As in the earlier embodiment, the proximal portion 60 of helical wire 58 is left exposed so that it may be electrically contacted. The connection hub 174 of the embodiment shown in FIG. 9 is able to frictionally engage the proximal end of the catheter 54 especially the portion of the catheter sheath 56 adjacent the proximal end 60 of the helical wire. The connection hub 174 slidably receives and frictionally holds the proximal end of the catheter 56. The electrical connector 176 is formed from a conductive material and acts as a physical and electrical connector between the electrical cable 172 and the catheter stylet 178 which in turn is electrically in contact with much of the length of the helical coil 60 and the safety ribbon wire 57. The electrical connector 176 is completely surrounded and rigidly held by the connection hub 174, which is made of an insulating material. Insulated connection wire 172 is also rigidly connected to the electrical connector 176 at connection point 180. Thus, the connection wire 172 allows an electrical voltage to be conducted from the connection plug 170 to the electrical connector 176 and the helical wire 58. The connection plug is dimensioned so as to be able to be connected to a voltage source such as the nerve stimulator 17 (FIG. 1).

The proximal end of central stylet 178 is rigidly connected to electrical connector 176 at point 182 and extends, when the catheter is frictionally retained by the connection hub 174, through the central bore 66 of the catheter 54 for the majority of the length of the catheter 54. Stylet distal end 179 is shown in FIG. 9. The central stylet is a long wire structure which is of such a material so as to provide extra rigidity to the catheter during the time when such rigidity is needed, i.e. prior to and during insertion of the catheter 54.

Note in FIG. 9 that, because the catheter 54 is retained in the connection hub 174, central stylet 178 and ribbon wire 57 are both present in the catheter lumen 66. Central stylet 178 extends from where it attaches to electrical connector 176 at point 182 to its distal end 179 not rigidly attached to any other structure. Ribbon wire 57, as described above, has a distal end rigidly connected to distal tip 72 and a proximal end rigidly connected to the proximal end 60 of the catheter assembly 54.

As in the earlier described embodiment, the distal portion 64 of the helical wire 58 is short relative to the remainder of the catheter assembly 54 and not covered by the catheter sheath 56. Attached to the distal end of the catheter 54 is conductive distal tip 72 which is a piece of rounded metal. Conductive distal tip 72 is electrically contacted to the nerve stimulator through the intervening structures, whether through the wire coil 58 or the ribbon wire 57.

Figure 8:
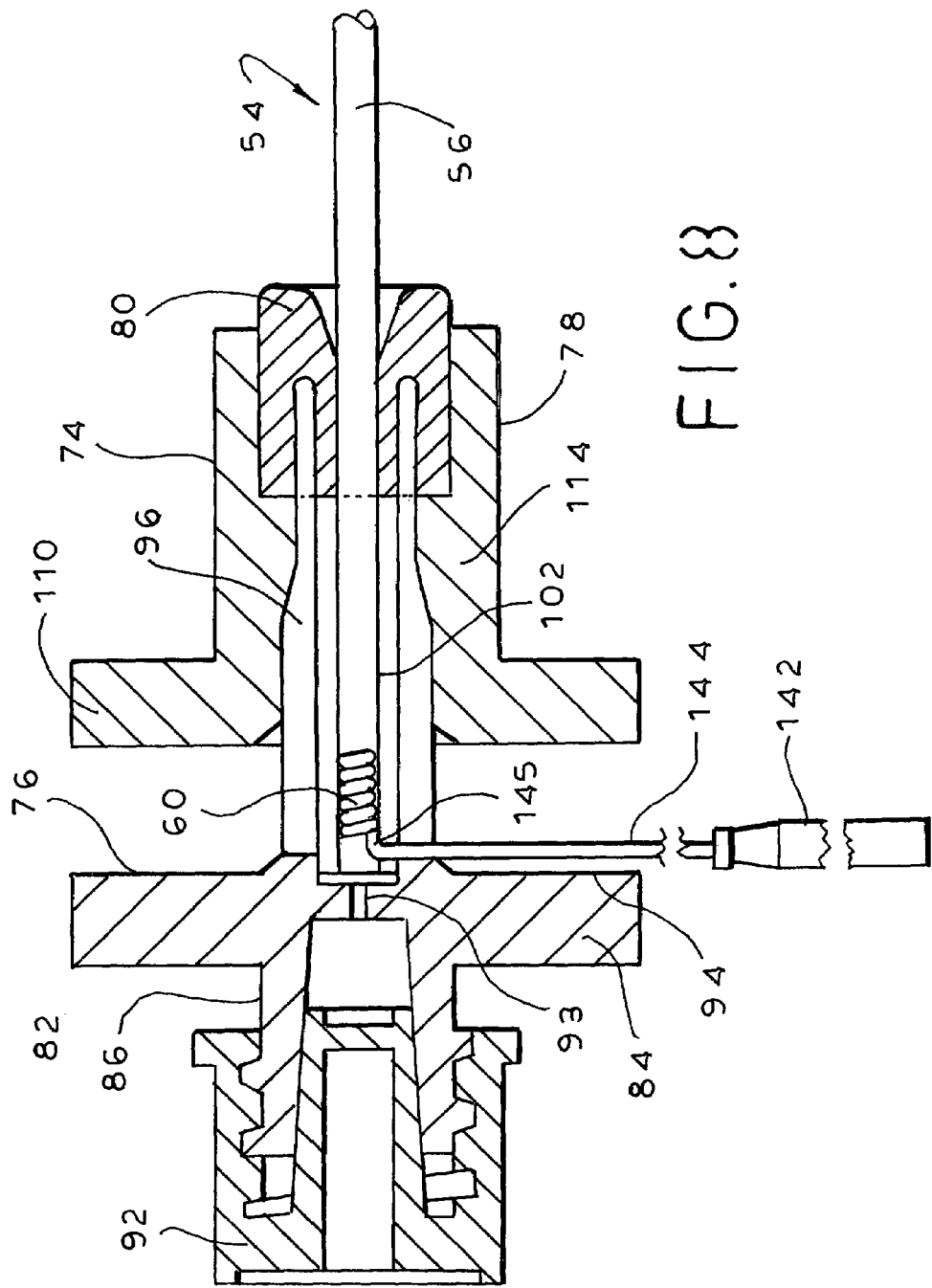
FIG. 8 is a side cross-sectional view of an alternate embodiment of the multipurpose connector in section, with the proximal end of the catheter inserted therein but not yet rigidly held in place.

Referring next to FIGS. 7 and 8, there is shown a catheter adapter 74. Accessing the central bore 66 of the catheter assembly 54 would be difficult given the diameter of this structure. This being the case, a catheter adapter 74 is used to provide access to the central bore 66 of the catheter assembly 54 for various delivery vehicles, e.g. a syringe, for the controlled delivery of fluid through the catheter.

The main constituents of the catheter adapter are the rear body 76, the front body 78 and the holding hub 80. The rear body 76 has a central flange 82. From the rear face 84 of the central flange 82 extends a connection cylinder 86. The function of this cylinder 86 is to facilitate attachment of a source of fluid to allow controlled delivery of the fluid to the central bore 66 of the catheter assembly 54. The end cap 92 provided over the connection cylinder 86 is primarily for sterility purposes and is simply removed after the catheter adapter 74 is attached to the catheter assembly 54. The central flange 82 has, at its center, a bore 93 passing completely therethrough such that the rear face 84 and front face 94 are in fluid communication.

From the central flange 84 extends an operating cylinder 96. The front body portion 78 of the catheter adapter 74 is disposed about the operating cylinder 96. In many ways, the operation of the catheter adapter depicted in FIGS. 7 and 8 is identical to the operation of the catheter adapter discussed previously and depicted in FIG. 4. One difference in the embodiment depicted in FIGS. 7 and 8 is that a connection wire 144 passes through the operating cylinder 96. This connection wire 144 is insulated except where it enters the operating cylinder 96. Thus, when the proximal end 60 of the catheter 54 is disposed in the central bore 102 of the operating cylinder 96, the wire coil 58 and/or the ribbon wire 57 of the catheter 54 are brought into electrical contact with the connection wire 144, either directly or through an intervening conducting structure, e.g. like a metal nut or washer. The end of the connection wire 144 which extends outside the operating cylinder 96 is connected to a connection plug 142 which can be plugged into a device 17 for supplying a stimulating voltage.

FIG. 10A discloses an alternative embodiment of the distal end 64 of the catheter assembly 54. Disclosed previously is that the insulating thermoplastic sheath 56 ends prior to the distal end 64 of the catheter and the helical wire coil 58 opens its helix 68 before it terminates at conductive distal tip 72. In the alternative embodiment of FIG. 10A the conductive distal tip 72 is replaced with a slug type distal tip 150. The insulating thermoplastic sheath 56 of the catheter assembly 54 extends past, i.e. distally of, the distal end of the wire helix 58. The slug type distal tip 150 has three main sections of respectively increasing diameter; the cylinder 158 sized to receive the wire coil 58, the center cylinder 156 sized to receive the thermoplastic sheath 54 and the distal cylinder 157 which is of greater diameter than either the inside diameter of the thermoplastic sheath 56 or the wire coil 58 thus avoiding being inserted too far into the catheter 54. Passage 152 passes entirely through the slug type distal tip 150, exiting at the distal exit 154 of the slug type distal tip 150. Thus, the central bore 66 of the catheter assembly 54 is still provided with an outlet through which medicine or other fluids can pass.

FIG. 10B shows a cross section of helical wire 58 having disposed thereon a thin layer of insulating material 59, e.g. PTFE (TEFLON). The thin layer of insulating material 59 can be disposed over the entire surface of the wire either before or after the wire is formed into a helix. The portions of the helical wire 58 that are desired to be exposed and, thus, capable of conducting electricity beyond the wire helix, may be easily stripped of the thin insulating coating 59 by any of a number of standard methods.

Figure 10C:
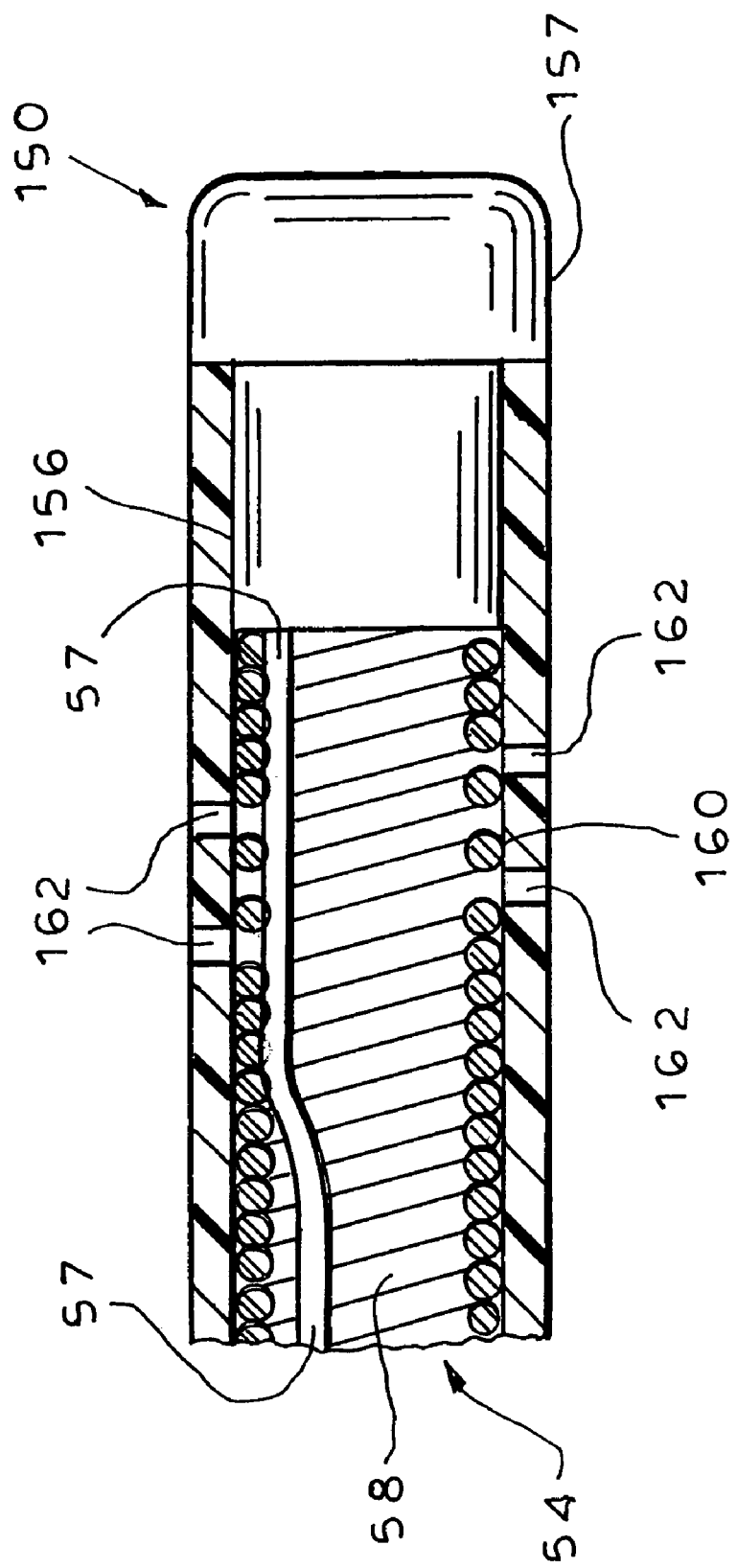
FIG. 10C is a side elevational detail of an alternate embodiment of the slug type distal tip shown inserted into the distal end of an alternate version of the catheter, the catheter is in section.

Shown in FIG. 10C is an alternative embodiment of the slug type distal tip 150. Here the passage 152, cylinder 158 and distal exit 154 of the slug type distal tip 150 are eliminated. Thus, the slug type distal tip 150 is solid and cannot pass fluid therethrough. A slight modification of the wire coil 58 and thermoplastic sheath 56 allow passage of the fluid. As seen in FIG. 10C, the helix of the wire coil 58 is again opened 160 as in other embodiments, e.g. FIG. 9, and radial channels 162 are formed in the thermoplastic sheath 58 adjacent the open helices 160. Thus, fluid flow would be allowed from the central bore 66 of the catheter 54 out through the open helices 160 and through the radial channels 162 into the patient.

In either embodiment shown in FIG. 10A or FIG. 10C, the ribbon wire 57 can either be rigidly connected to the proximal end of slug type distal tip 150 or rigidly connected to the distal end of wire helix 58. Any configuration which allows the wire helix and/or the ribbon wire to conductively contact slug type distal tip 150 is appropriate.

Included in the advantages of the slug type distal tip 150 is the concentration of the applied voltage in a specific location. The actual portion of the slug type distal tip 150 which is electrically conducting is relatively small when compared with other embodiments, where both the wire helix 58 and the conductive distal tip 72 were made of conductive materials. This concentration of the applied voltage should result in easier and more precise placement of the catheter and, thus, the fluid supplied by said catheter. In addition, as with any other electrically conducting structure described herein, it is possible to apply a thin layer of insulating material such as PTFE to the surface of the slug type distal tip 150 and then remove the insulating material from specific portions thereof.

FIGS. 11-15 disclose one embodiment for a cylindrical catheter lock 200 for use with the above described device. The function of the catheter lock 200 is to allow the catheter 54 to pass freely through the central bore of the catheter lock until it is desired to have the catheter firmly grasped by the catheter lock. This firm grasping by the catheter lock 200 of the catheter 54 is accomplished by an actuation of the catheter lock, the structure and functioning of which will be described in detail below.

Catheter lock 200 is made up of four main components. Stationary cylinder 202 is the portion of the catheter lock which supports the remaining components; stationary cylinder 202 is comprised of a large diameter portion 213 and a lesser diameter portion 214, which is coaxial with the large diameter portion 213. Rotatable cylinder 204 is disposed over the lesser diameter portion 214 of stationary cylinder 202. Compressible sleeve 208 is fully contained within the central bore of the lesser diameter portion 214 of the stationary cylinder 202. Finally, the fourth main component is the compressing cylinder 210 which is disposed in hole 216 in the lesser diameter portion 214 of the stationary cylinder 202.

Stationary cylinder 202 has an axial bore extending through its entire length. The axial bore in the lesser diameter portion 214 of the stationary cylinder 202 is sized to fit the compressible sleeve 208. The axial bore 218 in the remainder of the stationary cylinder 202 is sized to slidably fit the catheter 54. The axial bore in the rotatable cylinder 204 is sized to fit the lesser diameter portion 214 of the stationary cylinder 202. A recess 212 in the inner wall of the rotatable cylinder 204 is sized to fit a portion of the compressing cylinder 210.

When the components of the catheter lock 200 are fit together in the unlocked position shown in FIGS. 11 and 13, the compressing cylinder 210 is located in the hole 216 in the lesser diameter portion 214 of the stationary cylinder 202. The resilient nature of the compressible sleeve 208 causes the compressing cylinder 210 to be forced up into the recess 212 when the two are in alignment, as in the unlocked position. In the unlocked configuration the catheter lock 200 can freely slide along the catheter 54.

The catheter lock 200 may be twisted, made easier by a flat gripping portion 206 on the surface of the rotatable cylinder 204, to a locked position shown in FIGS. 12 and 14. In the locked position the hole 216 in the lesser diameter portion 214 of the stationary cylinder 202 and the recess 212 in the rotatable cylinder 204 are not in radial alignment. Thus, the compressing cylinder 210 overcomes the resilience of the compressible sleeve 208 by the inner wall of the rotatable cylinder 204, such that the compressible sleeve 208 is compressed by the compressing cylinder 210 when the rotatable cylinder is rotated into the locked position. When compressed in this way, the contact between the compressible sleeve 208 and the catheter 54 becomes much more firm, such that the frictional force needed to move these elements relative to each other is much higher that it was in the unlocked position and not easily overcome.

A second embodiment of the catheter lock 300 is shown in FIGS. 16-20. This catheter lock has a stationary portion 302 provided with an actuating cylinder 314. A bore extends through the stationary portion 302 of a diameter at least large enough to accommodate catheter 54. The portion of the bore extending through the actuating cylinder is also large enough to accommodate compressible sleeve 308. Compressible sleeve 308 has, itself, a bore capable of slidably receiving catheter 54. The lesser diameter bore of stationary portion 302 is coaxial with the bore of compressible sleeve 308 when disposed in the actuating cylinder 314. Thus, catheter 54 is capable of passing through the catheter lock 300.

The actuating cylinder 314 is provided with axial slots 316 therein as well as protrusions 315 thereon. Rotatable cylinder 304 has a central bore capable of receiving actuating cylinder 314 therein. The cross section of the central bore of the rotatable cylinder 304 receives not only the actuating cylinder 314 but also the protrusions 315 on the surface thereof, i.e. the bore has radially larger portions 312 to accommodate the protrusions 315 as well as rounded portions 313 to receive the remainder of the actuating cylinder, at least in the unlocked position shown in FIGS. 16 and 18.

However, since the protrusions 315 are only on certain portions of the actuating cylinder 314, rotation of the rotatable cylinder 304 with respect to the actuating cylinder will cause the rounded portions 313 to compress the protrusions into the bore of the actuating cylinder. This rotation will put the catheter lock 300 into its locked position. The compression of the protrusion 313 will cause compression of the compressible sleeve 308 and the contact between the compressible sleeve 308 and the catheter 54 to become much more firm, such that the frictional force needed to move these elements relative to each other is much higher that it was in the unlocked position and not easily overcome.

Peg 322 on the catheter lock 300 fits into groove 320. This serves the dual purposes of indicating to the user when the catheter lock 300 is either locked or unlocked and preventing over-rotation of the rotatable portion 304 of the catheter lock 300 with respect to the stationary portion 302.

In the embodiment shown in FIG. 24, the catheter lock 300 is attached to the proximal end of plastic needle hub 22. This attachment can be accomplished in a number of ways. It may be useful to have the catheter lock 300 permanently attached to the plastic needle hub 22. Thus, catheter lock could be physically welded, glued or otherwise permanently attached to the plastic needle hub. Alternatively, catheter lock 300 could be provided with an integral connector 330 capable of mateable, removable connection to the plastic needle hub 22. Along similar lines, FIGS. 25A and 25B disclose integral connectors 330 on catheter lock 300 capable of mateably, removably connecting to suitable structures which could easily be supplied on plastic needle hub 22. Numerous such connectors are well known in the art. Of course, catheter lock 200 could be substituted in the alternate embodiment shown in FIG. 24.

U.S. Pat. No. 5,830,151 to Hadzic et al. discloses "APPARATUS FOR LOCATING AND ANESTHETIZING PERIPHERAL NERVES A METHOD THEREFOR" and is incorporated herein by reference. The Hadzic Patent discloses an apparatus which allows an operator to control the electrical impulse output of a nerve stimulator generally similar to the nerve stimulator 17 discussed above. This control is accomplished by way of a foot pedal.

Figure 26:
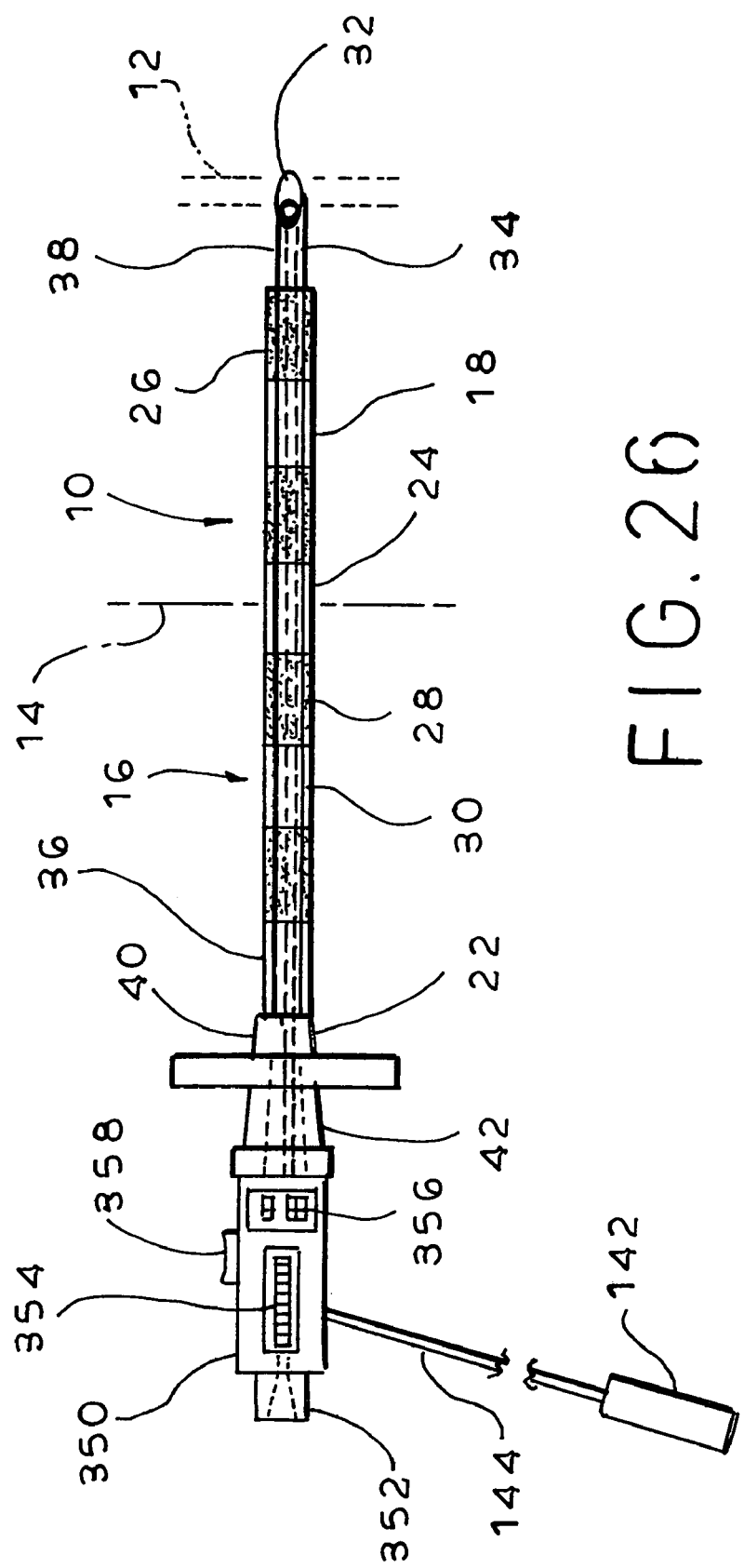
FIG. 26 is a side elevational view of one embodiment of the needle hub extension for supporting structures used in controlling the electrical impulse being supplied to the patient.

In an alternate embodiment of the present invention, a potentiometer for controlling the electrical impulses from the nerve stimulator 17 is provided on the needle hub 22 or an extension thereto. Such an extension 350 to needle hub 22 is illustrated in FIG. 26. Extension 350 can be integral to the needle hub 22 or connected thereto in any of a number of ways, including those discussed above relative to attaching the catheter lock to needle hub 22. The impulse control of the potentiometer for controlling nerve stimulator 17 can take the form of any conventional switch, e.g. a wheel type switch 354. Actuation of wheel switch 354 may control the relationship between the signal provided by the nerve stimulator and forwarded to the needle. The impulse control switch may also send a signal through wire conduit 144 to nerve stimulator 17 to increase or decrease the electrical impulse strength provided by the nerve stimulator to the needle. Additionally, a display 356 may also be supported on the extension 350. This display can take any form understandable to the user as conveying information regarding the electrical impulse being applied to the distal tip of the stimulating needle 18. This display 356 can be a simple digital readout or a group of LED elements. In addition, the display 356 can present information as to the electrical impulse being supplied by nerve stimulator 17 or be a feedback, i.e. monitoring the effect of the electrical impulse on the targeted tissue 10 of the patient. This feedback may be accomplished by connecting display 356 to the targeted tissue 356 of the patient by a wire otherwise insulated from the input electrical impulse.

Switch 358, also capable of being provided on extension 350, is either a mechanical or electrical switch capable of controlling the input of medicament or anaesthetic from an apparatus (not shown) connected to the connecting portion 352 of extension 350. The apparatus containing the medicament to be applied to the target nerve 12 of the patient can take numerous forms including a pump or spring loaded syringe.

The combination of the above disclosed structures directly on or adjacent to the needle hub 22 allows the medical practitioner to focus their entire attention on the most critical aspect of a procedure of this type, i.e. proper insertion of the needle 18. There is no need for the practitioner to be distracted, either by looking away from the needle or verbally directing an assistant to increase or decrease the electronic stimulation or report as to the current strength of the stimulation being applied. In addition, when the needle is properly placed, medicament may be applied by the practitioner without removing a hand from the needle hub 22 which may result in an unintended shift in the placement of the needle tip.

The above described apparatus may be used in a number of different medical procedures. The following described medical procedure is one type which utilizes the features embodied in the above described apparatus. The method is drawn to the correct placement of the catheter assembly 54 and, more particularly, the distal portion 64 thereof. Once the distal portion 64 of the catheter assembly 54 is determined to be in the correct position, a continuous interscalene nerve block may be administered.

The patient is positioned in the dorsal recumbent position with the head slightly in extension and turned somewhat to the opposite side. An assistant applies light traction on the arm with the elbow flexed.

The interscalene groove is easily palpated in this position by the following procedure: First, the posterior edge of the clavicular head of the sternocleidomastoid muscle is located; then the palpating fingers are placed postero-lateral to this muscle to identify the interscalene groove. The external jugular vein almost always lies directly superficial to the interscalene groove and provides a useful additional landmark. Needle entry should be anterior or posterior to the vein. Another constant finding is that the interscalene groove is approximately 3 cm lateral to the most prominent portion of the belly of the sternocleidomastoid muscle at the level of the cricoid cartilage.

The needle assembly 16 is inserted into the interscalene groove at the level of the cricoid (C6 level) and the needle is directed perpendicular to the skin in all the planes. For the placement of the catheter assembly 54 for this continuous interscalene nerve block technique, the needle assembly 16 enters the skin at a point approximately halfway between the mastoid and the clavicle, posterior to the posterior border of the clavicular head of the sternocleidomastoid muscle.

The point of needle entry is just caudal to the accessory nerve and just posterior to the anterior border of the posterior triangle of the neck. The accessory nerve can usually be identified by stimulating percutaneously with the electrical connector 52 of the nerve stimulator 17 since the nerve runs superficial to the fascial carpet of the posterior triangle of the neck, approximately midway between the clavicle and the mastoid. When the needle tip 32 is proximate the accessory nerve and voltage from the nerve stimulator 17 is applied, contractions of the trapezius muscle and elevation of the shoulder girdle will occur. The needle assembly 16 is directed caudal and parallel to the vertebrae aiming for the interscalene groove with the bevel of the needle assembly 16 directed laterally (outwards) to avoid possible central (epidural) placement of the catheter.

During insertion of the needle assembly, voltage should be continuously applied to the needle tip 32 as an aid in navigating the various nerves which may be encountered. The nerves to the levator scapula and rhomboid muscles may be encountered with the needle tip 32 at an early point. Stimulation of these nerves will also cause movement of the shoulder girdle when stimulated by elevating or rotating the scapula. The phrenic nerve, situated on the belly of the anterior scalene muscle, may be encountered. This causes unmistakable twitching of the ipsilateral diaphragm. All these nerves should be avoided by redirection and/or reinsertion of the needle assembly 16 as stimulation of these nerves can provide false indications of correct needle placement that will most certainly lead to block failure or phrenic nerve paralysis if local anesthetic agent is injected at this stage.

When the brachial plexus is encountered, definite and unmistakable muscle twitchings should be observed in the biceps and deltoid muscles of which the biceps movements are more easily seen. This is the reason for keeping the elbow slightly flexed during the procedure. If the phrenic nerve is accidentally stimulated the needle assembly 16 is pulled back slightly and the needle tip 32 is directed slightly posteriorly until the brachial plexus is encountered. As the needle tip 32 is advanced further a distinct "pop" or give can be felt followed by an increased intensity of the biceps and deltoid muscle twitchings. This is when the fascia sheath of the brachial plexus is penetrated and the tip of the needle 32 is now in direct contact with the brachial plexus. If removable electrical connector 52 is being utilized, it may be removed from the needle 18 at this time. Otherwise, electrical impulses being supplied to the needle 18 are merely switched off.

The central stylet 20, if present, is removed from the needle 18 and the catheter assembly 54, if not yet contained in the needle bore, is fed through the needle 18 to a point just past the tip of the needle 32. Such a placement of the conductive distal tip 72 is far enough so that the metal helical wire 58 does not make contact with the needle, i.e. the needle tip 32 is in contact with the catheter sheath 56 which will not conduct (disperse) electricity. The catheter adapter 74 can be attached to the proximal end 60 of the catheter assembly 54 at this point, if it has not been attached previously. The electrical connector 52 of the nerve stimulator 17 is then clipped to the tab portion 134 of the metal washer 130 provided on the catheter adapter 74. In an alternate embodiment of the apparatus, the connection plug 142 attached to the wire 144 in contact with the catheter adapter 74 is plugged into the nerve stimulator 17.

The output of the nerve stimulator 17 can be turned down (typically to approximately 0.5-1.0 mA) as the muscle twitching will increase because all the current is now concentrated in the unsheathed helix tip 72 of the catheter assembly 54. In an alternate embodiment of the apparatus the current is even more concentrated at the slug type distal tip 150. Muscle contractions with a nerve stimulator 17 output of approximately 0.5 mA provides additional proof of proper placement into the sheath.

Advancement of the catheter helical tip 72 or slug type distal tip 150 approximately an additional 1 cm beyond the tip of the needle 32 down the brachial plexus sheath should not result in a decreasing of the twitching in the biceps and deltoid muscles. Frequently, though, the muscle twitchings do decrease in which case the needle and catheter complex 16, 54 are simultaneously pulled back slightly as a unit, until maximal twitchings are again observed. The catheter 54 is then again advanced and the above process is repeated until maximal twitchings are observed during catheter 54 advancement. It is most important for guaranteed successful catheter placement to observe maximal muscle contractions while catheter is being advanced. The catheter 54 frequently cannot be fed beyond the coracoid process. It should, however, not be forced further as this may lead to nerve damage and, for shoulder surgery, it is not necessary to advance the catheter beyond this point. The needle assembly 16 may then removed and the catheter securely fixed.

Indwelling interscalene catheters are notorious for falling out or dislodging. To avoid dislodgment after placement of the catheter, the same needle 16 used to place the catheter, is inserted subcutaneously from just above the suprasternal notch and directed superolaterally, avoiding vascular structures, towards the point of entry of the catheter. The needle assembly 16 is advanced to exit through the same orifice in the skin as the catheter 54 and just next to the catheter. The proximal end of the catheter 60 is fed from the tip of the needle 32 through the needle 18 and the needle is removed so that the catheter 54 is tunneled subcutaneously. Kinking of the catheter should be avoided as the elbow formed by the catheter disappears under the skin. The catheter is then covered with a transparent dressing.

As an alternative to the use of the needle 16 in the tunneling procedure, a specialized device may be utilized. FIG. 23 shows such a specialized device. Tunneler 400 is provided with a gripping hub 402 which is connected to a tunneler stylet 407 or other sharp instrument. A tunnel sheath 410 covers the stylet over the majority of its length. When it is desired to create a tunnel that will assist in holding catheter 54, the tunneler 400 is utilized. The tunnel will typically begin somewhere near the site where the catheter 54 exits the body of the patient. Thus, the tip of tunneler stylet 407 is inserted at this site and tunneled away from the exit site, until it is desired to end the tunnel, at which point the tip of tunneler stylet 407 is caused to exit the patient. Once the tunnel is created, the tunneler may be removed while the tunnel sheath 410, being completely separable from the gripping hub 402 and the tunneler stylet, remains subcutaneously tunneled inside the patient. At this point the catheter 54 may be inserted into the end of the sheath closest to the first catheter exit site. The catheter 54 is easily fed through the tunnel sheath 410 until it exits the other end of the tunnel sheath 410. The tunnel sheath 410 may then be pulled out of the patient, leaving the catheter 54 subcutaneously tunneled, as above.

An additional feature shown in FIG. 23 is skin bridge 406. Skin bridge 406 has a central hole 409 which initially allows tunneler sheath 410 to retain the skin bridge 406. After the tunneler stylet 407 is removed, as discussed above, the catheter 54 is then disposed through the hole 409. The tunneler sheath may then be pulled out of the patient, leaving the catheter 54 subcutaneously tunneled, as above. Because of the placement of the skin bridge adjacent the proximal end of the tunneler 400 and the fact that the tunneler is of the forward type, the skin bridge will be retained by the catheter directly adjacent the original exit site of the catheter 54, i.e. between the original exit and the subcutaneous tunnel. Skin bridge 406 allows increased stability of the catheter placement when anchored to the skin of the patient using standard methods. In addition, skin bridge 406 may be used as a handle for removing the catheter 54 from the patient or merely from the subcutaneous tunnel.

With the catheter assembly thus firmly in place, anaesthetic may be administered to effectuate a nerve block:

1. When a dense motor and sensory block is required:
    a) Ropivacaine 10 mg/mL (1%). Inject 20 mL as a bolus and then infuse with syringe driver a diluted concentration (5 mg/mL or 0.5%) at 10-20 mL/hour. Or
    b) Bupivacaine 5 mg/mL (0.5%). Inject 20 mL as a bolus and then infuse a diluted concentration (2.5 mg/mL or 0.25%) at 10-20 mL/hour.
2. When sensory block with minimal motor block is required:
    a) Ropivacaine 2 mg/mL (0.2%). Inject 10-20 mL as a bolus and then infuse the same concentration at 1-10 mL/hour. Continually adjust (titrate) the infusion rate to achieve the desired effect. Or
    b) Bupivacaine 2.5 mg/mL (0.25%). Inject 10-20 mL as a bolus and the infuse the same concentration at 1-10 mL/hour. Continually adjust (titrate) the infusion rate to achieve the desired effect.
3. Patient Controlled Interscalene Nerve Block:
    Injection if a bolus of 30 mL bupivacaine (0.4%) via an indwelling catheter into the brachial plexus sheath at the level of the interscalene groove followed by a background infusion of bupivacaine 0.15% at a rate of 5 mL/hour and a patient-controlled bolus of 4 mL for patients weighing >65 Kg and 3 mL for patients weighing <65 Kg. A lockout time of 20 minutes was programmed into the PCA device. This seemed successful. Promising preliminary results have been achieved with ropivacaine. It seems that finer adjustment of the block to achieve varying levels and densities of motor and sensory blockade may be possible with ropivacaine.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A medical-surgical instrument comprising:
    a. a needle having a central bore for providing access to a nerve of a patient and a needle hub disposed about a proximal end of the needle;
    b. a catheter for providing fluid flow access to and electrically stimulating the nerve of the patient, the catheter capable of being inserted into the patient through the needle; and c. a catheter lock attached to the needle hub for selectively holding said catheter stationary with respect to said needle or allowing said catheter to slide through said catheter lock and said needle, said catheter lock comprising a bore and an actuating portion, the catheter being inserted through the bore of the catheter lock and the needle central bore such that actuation of the actuating portion of the catheter lock causes the catheter lock to frictionally hold the catheter in place with respect to the catheter lock, the catheter lock frictionally holding the catheter at one of a plurality of locations along the length of the catheter.

2. The medical-surgical instrument of claim 1, wherein the needle further comprises a wire with a first end attached to a proximal end of the needle and a second end adapted to be connected to a source of electricity, for conveying electricity provided by the source of electricity to the needle.

3. The medical-surgical instrument of claim 1, wherein the catheter is inserted through the catheter lock and needle such that a distal tip of the catheter extends beyond a distal end of the needle.

4. The medical-surgical instrument of claim 1, wherein the catheter additionally comprises a central bore capable of bringing a liquid from a proximal end of the catheter to the nerve of the patient.

5. The medical-surgical instrument of claim 1, wherein the needle additionally comprises an electrically insulating covering on an outer surface of the needle.

6. The medical-surgical instrument of claim 1 wherein a proximal end of the catheter is inserted into and frictionally held by a catheter adapter, whereby a fluid delivery apparatus to supply a fluid to said catheter is attached to the catheter adapter.

7. The medical-surgical instrument of claim 1 wherein a proximal end of the catheter is inserted into and frictionally held by a catheter adapter, whereby a source of electricity to supply electricity to said catheter is conductively attached to the catheter adapter.

8. The medical-surgical instrument of claim 1 wherein the catheter further comprises support means for supporting the catheter.

9. The medical-surgical instrument of claim 8 wherein the support means comprises a helical wire underlying the catheter.

10. The medical-surgical instrument of claim 9 wherein the support means is electrically conducting.

11. The medical-surgical instrument of claim 1, wherein the catheter lock is removably attached to the needle.

12. The medical-surgical instrument of claim 11 wherein direct fluid injection through the needle hub may be achieved after removing the catheter lock.

13. A medical-surgical instrument comprising:
a. a needle having a central bore and a hub disposed about a proximal end of the needle;
b. a catheter having a proximal end, a distal end, an electrically conducting distal tip, and a lumen for allowing fluid flow through the catheter, the catheter adapted to conduct electricity from the proximal end of the catheter to the distal tip of the catheter;
c. a catheter lock comprising a bore and an actuating portion; and
d. the catheter being inserted through the bore of the catheter lock and the needle central bore such that actuation of the actuating portion of the catheter lock causes the catheter lock to frictionally hold the catheter in place with respect to the catheter lock, the catheter lock frictionally holding the catheter at one of a plurality of locations along the length of the catheter.

14. The medical-surgical instrument of claim 13, wherein the catheter further comprises a bore for conveying a liquid.

15. The medical-surgical instrument of claim 14, wherein the catheter further includes a liquid exit proximate the distal tip for allowing delivery of a liquid to a patient proximate the distal tip of the catheter.

16. The medical-surgical instrument of claim 14, wherein the catheter further includes a liquid exit as an integral part of a distal tip of the catheter for allowing delivery of a liquid to a patient through the distal tip of the catheter.

17. The medical-surgical instrument of claim 13, wherein the catheter further comprises a conducting wire extending from the proximal end of the catheter to the electrically conducting distal tip of the catheter.

18. The medical-surgical instrument of claim 13, wherein the conducting wire is approximately parallel with the catheter in an axial direction for a majority of the length of the conducting wire.

19. The medical-surgical instrument of claim 13, wherein the conducting wire is helically shaped.

20. The medical-surgical instrument of claim 13, wherein the catheter comprises an electrically insulating thermoplastic sheath and a supporting structure disposed in supporting contact with the thermoplastic sheath along at least substantially the entire length of the thermoplastic sheath.

21. The medical-surgical instrument of claim 20 wherein the supporting structure is a helical wire.

22. The medical-surgical instrument of claim 21 wherein the helical wire is electrically conducting.

23. The medical-surgical instrument of claim 13, the catheter lock further comprising:
a. a stationary body portion attached to the hub and extending proximally therefrom;
b. the actuating portion comprising a rotatable body portion rotatably engaged with the stationary body portion; and
c. means for firmly grasping a portion of the catheter disposed through the bore of the stationary body portion, said means being engaged and disengaged by the actuating portion.

24. The medical-surgical instrument of claim 23, wherein the catheter additionally comprises a central bore capable of conveying a liquid along substantially the entire length of the catheter.

25. The medical-surgical instrument of claim 23, wherein the needle additionally comprises an outer surface between the proximal end and a distal end of the needle, a portion of the outer surface of the needle being covered in an electrically insulating covering.

26. The medical-surgical instrument of claim 23, further comprising a conducting wire extending from the proximal end of the catheter to the distal end of the catheter and conductively connected to the distal tip.

27. The medical-surgical instrument of claim 26, wherein the conducting wire is substantially parallel to the axis of the catheter.

28. The medical-surgical instrument of claim 26, wherein the conducting wire is connected to the proximal end of the catheter.

29. The medical-surgical instrument of claim 23 wherein the catheter comprises an electrically insulating thermoplastic sheath and a supporting structure disposed in supporting contact with the thermoplastic sheath along at least substantially the entire length of the thermoplastic sheath.

30. The medical-surgical instrument of claim 29 wherein the supporting structure is a helical wire.

31. The medical-surgical instrument of claim 30 wherein the helical wire is electrically conducting.

32. The medical surgical instrument of claim 30 wherein the helical wire extends distally of the thermoplastic sheath such that the distal end of the catheter comprises the helical wire not covered by the thermoplastic sheath.

33. The medical-surgical instrument of claim 30 wherein a conducting wire is conductively connected to the helical wire near the proximal end of the catheter.

34. The medical-surgical instrument of claim 30 wherein the helical wire extends proximally of the thermoplastic sheath such that the proximal end of the catheter comprises the helical wire not covered by the thermoplastic sheath.

35. The medical-surgical instrument of claim 30 wherein the proximal end of the catheter is received within catheter adapter means for allowing connection of a fluid delivery apparatus.

36. The medical-surgical instrument of claim 30 wherein the proximal end of the catheter is received within catheter adapter means for allowing connection of a source of electricity to the proximal end of the catheter, the catheter adapter includes an insulated wire and connector adapted to be connected to a source of electricity.

37. The medical-surgical instrument of claim 13, further comprising an insulated wire, a first end of the insulated wire is conductively connected to the proximal end of the needle and a second end of the insulated wire is adapted such that it can be connected to a source of electricity, such that the needle is capable of conveying electricity provided by the source of electricity from the proximal end to a distal end of the needle.

38. The medical-surgical instrument of claim 13, wherein the catheter is inserted through the catheter lock and needle central bore such that the distal tip of the catheter extends beyond a distal end of the needle.

39. The medical-surgical instrument of claim 13, wherein the catheter lock is removably attached to the needle hub.

40. The medical-surgical instrument of claim 39 wherein direct fluid injection through the needle hub may be achieved after removing the catheter lock.

41. A medical-surgical instrument comprising:
   a. a needle having a central bore and a hub comprising a distal end disposed about a proximal end of the needle, the hub further comprising a proximal end;
   b. a catheter having a proximal end, a distal end and an electrically conducting distal tip, the catheter adapted to conduct electricity from the proximal end of the catheter to the distal tip of the catheter, the catheter further comprising a lumen permitting fluid flow through the catheter;
   c. a catheter lock comprising a bore and an actuating portion, the catheter lock being attached to the proximal end of the needle hub in such a way that the catheter lock is capable of easily being unattached from the needle hub; and
   d. the catheter being inserted through the bore of the catheter lock and the needle central bore such that actuation of the actuating portion of the catheter lock causes the catheter lock to frictionally hold, at one of a plurality of locations along the length of the catheter, the catheter in place with respect to the catheter lock.

42. The medical-surgical instrument of claim 41 wherein direct fluid injection through the needle hub may be achieved after removing the catheter lock.

* * * * *